US009944700B2

(12) United States Patent
Danahay et al.

(10) Patent No.: US 9,944,700 B2
(45) Date of Patent: Apr. 17, 2018

(54) NOTCH2 BINDING MOLECULES FOR TREATING RESPIRATORY DISEASES

(71) Applicants: Henry Luke Danahay, Horsham (GB); Aron Brandon Jaffe, Boston, MA (US)

(72) Inventors: Henry Luke Danahay, Horsham (GB); Aron Brandon Jaffe, Boston, MA (US)

(73) Assignee: NOVARTIS AG, Basel (CH)

( * ) Notice: Subject to any disclaimer, the term of this patent is extended or adjusted under 35 U.S.C. 154(b) by 17 days.

(21) Appl. No.: 14/774,816

(22) PCT Filed: Mar. 11, 2014

(86) PCT No.: PCT/IB2014/059627
§ 371 (c)(1),
(2) Date: Sep. 11, 2015

(87) PCT Pub. No.: WO2014/141064
PCT Pub. Date: Sep. 18, 2014

(65) Prior Publication Data
US 2016/0046710 A1    Feb. 18, 2016

Related U.S. Application Data

(60) Provisional application No. 61/779,195, filed on Mar. 13, 2013, provisional application No. 61/866,273, filed on Aug. 15, 2013.

(51) Int. Cl.
*A61K 39/395* (2006.01)
*C07K 16/28* (2006.01)
(Continued)

(52) U.S. Cl.
CPC .............. *C07K 16/28* (2013.01); *A61K 38/18* (2013.01); *A61K 2039/505* (2013.01); *A61K 2039/507* (2013.01); *C07K 2317/76* (2013.01)

(58) Field of Classification Search
None
See application file for complete search history.

(56) References Cited

U.S. PATENT DOCUMENTS 7,189,507 B2    3/2007 Mack et al.
8,226,943 B2 *  7/2012 Gurney ................ C07K 16/462
(Continued)

FOREIGN PATENT DOCUMENTS

EP    0662827 B2    1/2009
EP    2924051 A1    9/2015
(Continued)

OTHER PUBLICATIONS

Lange et al., Ventilatory function and chronic mucus hypersecretion as predictors of death from lung cancer, American Rev. Respiratory Dis. 141(3):613-617,1990, abstract only.*
(Continued)

*Primary Examiner* — Claire Kaufman
(74) *Attorney, Agent, or Firm* — Adam Poulin-Kerstien

(57) ABSTRACT

The balance and distribution of epithelial cell types is required to maintain tissue homeostasis. In the lung, perturbations of this balance are hallmarks of human respiratory diseases, including goblet cell metaplasia and enhanced mucus secretion in asthma and chronic obstructive pulmonary disease. We found that inflammatory cytokine treatment resulted in a skewing of basal cell differentiation towards a goblet cell fate, culminating in enhanced mucus production. We identified Notch2 as a key node required for cytokine-induced goblet cell metaplasia in vitro and in vivo Inhibition of Notch2 prevents goblet cell metaplasia induced by a broad range of stimuli, which is a hallmark of many respiratory diseases.

7 Claims, 13 Drawing Sheets

(51) Int. Cl.
*A61K 38/18* (2006.01)
*A61K 39/00* (2006.01)

(56) References Cited

U.S. PATENT DOCUMENTS

| | | | |
|---|---|---|---|
| 8,557,965 | B2 | 10/2013 | Saunders et al. |
| 8,563,269 | B2 | 10/2013 | Stagliano et al. |
| 8,709,710 | B2 | 4/2014 | Scheffold et al. |
| 2010/0080808 | A1* | 4/2010 | Siebel .................... C07K 16/28 |
| 2010/0189651 | A1 | 7/2010 | Stagliano et al. |
| 2011/0123532 | A1 | 5/2011 | Gurney et al. |
| 2012/0045458 | A1 | 2/2012 | Scheffold et al. |
| 2012/0149061 | A1 | 6/2012 | Stagliano et al. |
| 2012/0288496 | A1 | 11/2012 | Gurney et al. |
| 2013/0064832 | A1 | 3/2013 | Aikawa et al. |
| 2013/0089562 | A1 | 4/2013 | French et al. |
| 2013/0171124 | A1 | 7/2013 | Cong et al. |
| 2013/0253172 | A1 | 9/2013 | Gurney et al. |
| 2013/0296536 | A1 | 11/2013 | Gurney et al. |
| 2014/0286955 | A1 | 9/2014 | Aifantis et al. |
| 2014/0314749 | A1 | 10/2014 | French et al. |
| 2015/0132294 | A1 | 5/2015 | Clarke et al. |
| 2015/0266973 | A1 | 9/2015 | Jarjour et al. |
| 2015/0284455 | A1 | 10/2015 | Springer et al. |
| 2016/0030561 | A1 | 2/2016 | Hoey et al. |
| 2016/0053016 | A1 | 2/2016 | Lewicki et al. |
| 2016/0068596 | A1 | 3/2016 | de Sauvage et al. |

FOREIGN PATENT DOCUMENTS

| | | | |
|---|---|---|---|
| JP | 2013231018 | A | 11/2013 |
| WO | 1999004746 | A2 | 2/1999 |
| WO | 2002096952 | A2 | 12/2002 |
| WO | 2003012111 | A2 | 2/2003 |
| WO | 2004022730 | A1 | 3/2004 |
| WO | 2004030615 | A2 | 4/2004 |
| WO | 2004035732 | A2 | 4/2004 |
| WO | 2004041170 | A2 | 5/2004 |
| WO | 2004048938 | A2 | 6/2004 |
| WO | 2004073732 | A1 | 9/2004 |
| WO | 2004082710 | A1 | 9/2004 |
| WO | 2006135949 | A2 | 12/2006 |
| WO | 2007145840 | A2 | 12/2007 |
| WO | 2008057144 | A2 | 5/2008 |
| WO | 2008063849 | A2 | 5/2008 |
| WO | 2008091641 | A2 | 7/2008 |
| WO | 2008092445 | A2 | 8/2008 |
| WO | 2008108910 | A2 | 9/2008 |
| WO | 2009025867 | A2 | 2/2009 |
| WO | 2009124931 | A2 | 10/2009 |
| WO | 2010005566 | A2 | 1/2010 |
| WO | 2010039832 | A1 | 4/2010 |
| WO | 2010081173 | A2 | 7/2010 |
| WO | 2010091679 | A2 | 8/2010 |
| WO | 2013052155 | A1 | 4/2013 |
| WO | 2013074596 | A1 | 5/2013 |
| WO | 2013173542 | A1 | 11/2013 |
| WO | 2014039994 | A2 | 3/2014 |
| WO | 2014141064 | A1 | 9/2014 |

OTHER PUBLICATIONS

Milano et al., Modulation of Notch processing by gamma-secretase inhibitors causes intestinal goblet cell metaplasia and induction of genes known to specify gut secretory lineage differentiation. Toxicol. Sci, 82(1):341-358, Aug. 19, 2004.*

Blaumueller et al., " Intracellular cleavage of Notch leads to a heterodimeric receptor on the plasma membrane," Cell. Jul. 25, 1997;90(2):281-91.

"OncoMed Presents First-in-Human Phase I Data on Anti-Notch2/3 Antibody at ASCO," Jun. 2, 2012, retrieved from the Internet: URL: http://www.oncomed.com/releases/press_release_2012_06_02.pdf [retrieved on Aug. 17, 2016].

Guseh et al., "Notch signaling promotes airway mucous metaplasia and inhibits alveolar development," Development. May 2009;136(10):1751-9.

Kang et al., "Gamma-secretase inhibitor reduces allergic pulmonary inflammation by modulating Th1 and Th2 responses," Am J Respir Crit Care Med. May 15, 2009;179(10):875-82.

Tsao et al., "Notch signaling prevents mucous metaplasia in mouse conducting airways during postnatal development," Development. Aug. 2011;138(16):3533-43.

Tilley et al., "Down-regulation of the notch pathway in human airway epithelium in association with smoking and chronic obstructive pulmonary disease," Am J Respir Crit Care Med. Mar. 15, 2009;179(6):457-66.

Whitsett et al., "Notch and basal cells take center stage during airway epithelial regeneration," Cell Stem Cell. Jun. 3, 2011;8(6):597-8.

Antoniu, Monoclonal antibodies for asthma and chronic obstructive pulmonary disease, Expert Opin Biol Ther. Feb. 2013;13(2):257-68.

Wu et al., "Therapeutic antibody targeting of individual Notch receptors," Nature. Apr. 15, 2010;464(7291):1052-7.

"OncoMed Pharmaceuticals Initiates Phase 1b/2 Clinical Trial of Anti-Cancer Stem Cell Therapeutic OMP-59R5 (Anti-Notch2/3) in Small Cell Lung Cancer (SCLC) and Amends Phase 1b/2 Pancreatic Cancer Trial," May 14, 2013, retrieved from the Internet: URL:http://files.shareholder.com/downloads/AMDA-20K1SK/ 0x0x675682/d0fd1bf7-5edd-4aa2-8dca-e525ac9867a2/675682.pdf [retrieved on Aug. 17, 2016].

International Search Report and Written Opinion for International Application No. PCT/IB2014/059627, dated Jul. 10, 2014 (16 pages).

* cited by examiner (a)

(b)

(c)

(d)

(e)

(f)

(a)

(b)

(c)

(a)

(b)

(c)

(d)

(e)

(a)

(b)

(c)

(a)

(b)

SEQUENCE LISTING

<160> NUMBER OF SEQ ID NOS: 9

<210> SEQ ID NO 1
<211> LENGTH: 449
<212> TYPE: PRT
<213> ORGANISM: Artificial Sequence
<220> FEATURE:
<223> OTHER INFORMATION: Synthetic human sequence

<400> SEQUENCE: 1

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ala Pro Gly Lys Gly Leu Glu Trp Val
        35                  40                  45

Ala Arg Ile Asn Pro Pro Asn Arg Ser Asn Gln Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Phe Arg Trp Val Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

```
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
            435                 440                 445
Lys

<210> SEQ ID NO 2
<211> LENGTH: 214
<212> TYPE: PRT
<213> ORGANISM: Artificial Sequence
<220> FEATURE:
<223> OTHER INFORMATION: Synthetic human sequence

<400> SEQUENCE: 2

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Ser Thr Ala
            20                  25                  30
Val Ala Trp Tyr Gln Gln Lys Pro Asp Gly Thr Val Lys Leu Leu Ile
        35                  40                  45
Tyr Ser Ala Ser Phe Leu Tyr Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Phe Tyr Thr Thr Pro Ser
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 3
<211> LENGTH: 451
<212> TYPE: PRT
<213> ORGANISM: Artificial Sequence
<220> FEATURE:
<223> OTHER INFORMATION: Synthetic human sequence
```

```
<400> SEQUENCE: 3

Gln Val Gln Leu Val Glu Ser Gly Gly Gly Leu Val Gln Pro Gly Gly
  1               5                  10                  15

Ser Leu Arg Leu Ser Cys Ala Ala Gly Tyr Thr Phe Ser Ser Tyr Gly
             20                  25                  30

Met Ser Trp Val Arg Gln Ala Pro Gly Lys Gly Leu Glu Trp Val Ser
         35                  40                  45

Tyr Ile Tyr Pro Tyr Ser Gly Ala Thr Tyr Tyr Ala Asp Ser Val Lys
     50                  55                  60

Gly Arg Phe Thr Ile Ser Ala Asp Thr Ser Lys Asn Thr Ala Tyr Leu
 65                  70                  75                  80

Gln Met Asn Ser Leu Arg Ala Glu Asp Thr Ala Val Tyr Tyr Cys Ala
                 85                  90                  95

Arg His Ser Gly Tyr Tyr Arg Ile Ser Ser Ala Met Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
        450

<210> SEQ ID NO 4
<211> LENGTH: 214
<212> TYPE: PRT
<213> ORGANISM: Artificial Sequence
<220> FEATURE:
<223> OTHER INFORMATION: Synthetic human sequence

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Lys Arg Phe
            20                  25                  30

Leu Ala Trp Tyr Gln Gln Lys Pro Gly Lys Ala Pro Lys Leu Leu Ile
        35                  40                  45

Tyr Gly Ala Ser Thr Arg Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Arg Ser Pro His
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 445
<212> TYPE: PRT
<213> ORGANISM: Artificial Sequence
<220> FEATURE:
<223> OTHER INFORMATION: Synthetic human sequence

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30
```

```
Gly Met Ser Trp Val Arg Gln Ala Pro Gly Lys Gly Leu Glu Trp Val
        35                  40                  45

Ser Val Ile Ala Ser Ser Gly Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Ile Phe Tyr Thr Thr Trp Gly Gln Gly Thr Leu Val Thr
                100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
        435                 440                 445
```

```
<210> SEQ ID NO 6
<211> LENGTH: 215
<212> TYPE: PRT
<213> ORGANISM: Artificial Sequence
<220> FEATURE:
<223> OTHER INFORMATION: Synthetic human sequence

<400> SEQUENCE: 6

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ser Asn Phe Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 7
<211> LENGTH: 445
<212> TYPE: PRT
<213> ORGANISM: Artificial Sequence
<220> FEATURE:
<223> OTHER INFORMATION: Synthetic human sequence

<400> SEQUENCE: 7

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser His Tyr
            20                  25                  30

Tyr Met Ser Trp Val Arg Gln Thr Pro Glu Lys Arg Leu Glu Trp Val
        35                  40                  45

Ala Tyr Ile Ser Asn Gly Gly Gly Arg Thr Asp Tyr Pro Asp Ser Val
    50                  55                  60

Lys Gly Arg Phe Thr Ile Ser Arg Asp Asn Ala Lys Asn Thr Leu His
65                  70                  75                  80
```

```
Leu Gln Met Ser Ser Leu Lys Ser Glu Asp Thr Ala Met Tyr Tyr Cys
                85                  90                  95

Thr Arg Leu Asp Tyr Phe Gly Gly Ser Pro Tyr Phe Asp Tyr Trp Gly
            100                 105                 110

Gln Gly Thr Thr Leu Thr Val Ser Ser Ala Lys Thr Thr Pro Pro Ser
            115                 120                 125

Val Tyr Pro Leu Ala Pro Gly Ser Ala Ala Gln Thr Asn Ser Met Val
            130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
            195                 200                 205

Ala Ser Ser Thr Lys Val Asp Lys Lys Ile Val Pro Arg Asp Cys Gly
210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
            245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
            275                 280                 285

Pro Arg Glu Glu Gln Phe Asn Ser Thr Phe Arg Ser Val Ser Glu Leu
290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
            325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
            355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
            405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
            435                 440                 445

<210> SEQ ID NO 8
<211> LENGTH: 213
<212> TYPE: PRT
<213> ORGANISM: Artificial Sequence
<220> FEATURE:
<223> OTHER INFORMATION: Synthetic human sequence
```

<400> SEQUENCE: 8

Glu Ile Val Leu Thr Gln Ser Pro Ala Ile Thr Ala Ala Ser Leu Gly
1               5                   10                  15

Gln Lys Val Thr Ile Thr Cys Ser Ala Ser Ser Ser Val Ser Tyr Met
            20                  25                  30

His Trp Tyr Gln Gln Lys Ser Gly Thr Ser Pro Lys Pro Trp Ile Tyr
        35                  40                  45

Glu Ile Ser Lys Leu Ala Ser Gly Val Pro Pro Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu Ile Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 9
<211> LENGTH: 451
<212> TYPE: PRT
<213> ORGANISM: Artificial Sequence
<220> FEATURE:
<223> OTHER INFORMATION: Synthetic human sequence

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Gly Tyr Thr Phe Ser Ser Tyr Gly
            20                  25                  30

Met Ser Trp Val Arg Gln Ala Pro Gly Lys Gly Leu Glu Trp Val Ser
        35                  40                  45

Tyr Ile Tyr Pro Tyr Ser Gly Ala Thr Tyr Tyr Ala Asp Ser Val Lys
    50                  55                  60

Gly Arg Phe Thr Ile Ser Ala Asp Thr Ser Lys Asn Thr Ala Tyr Leu
65                  70                  75                  80

Gln Met Asn Ser Leu Arg Ala Glu Asp Thr Ala Val Tyr Tyr Cys Ala
                85                  90                  95

Arg His Ser Gly Tyr Tyr Arg Ile Ser Ser Ala Met Asp Val Trp Gly
            100                 105                 110

Gln Gly Thr Leu Val Thr Val Ser Ser Ala Ser Thr Lys Gly Pro Ser
        115                 120                 125

-continued

```
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
    275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly Lys
    450
```

NOTCH2 BINDING MOLECULES FOR TREATING RESPIRATORY DISEASES

RELATED APPLICATIONS

This application is a national phase entry under 35 USC § 371 of PCT Application No. PCT/IB2014/059627, filed on Mar. 11, 2014, which claims priority under 35 USC § 119 to U.S. Provisional Application Nos. 61/779,195, filed Mar. 13, 2013 and 61/866,273, filed Aug. 15, 2013, all of which are incorporated herein by reference in their entireties.

FIELD OF THE INVENTION

The invention is in the field of treatment of respiratory disease using a binding molecule against Notch2. In particular, it relates to the treatment of cystic fibrosis (CF), primary ciliary dyskinesia, chronic bronchitis, chronic obstructive pulmonary disease (COPD), asthma or respiratory tract infections using antibodies against Notch2. Such antibodies may be an antagonist anti-Notch2 antibody or a neutralizing antibody against Notch2 suitable for therapeutic uses.

BACKGROUND OF THE INVENTION

The lung epithelium has evolved to serve a number of functions ranging from gas exchange in the alveolus to the regulation of mucus clearance in the larger conducting airways. The heterogeneous mix of epithelial cell types enables these functions at the different levels of the airway. Airway epithelial cells include mucin producing and secreting goblet cells, which provide a mucus gel for the multi-ciliated cells to propel out of the airways, surfactant producing type 2 pneumocytes, which maintain alveolar patency with type 1 pneumocytes enabling gas exchange, and basal cells, the progenitor of the overlying epithelium (Rackley, C. R. & Stripp, B. R., The Journal of Clinical Investigation 122, 2724-2730 (2012)).

The protective role of the airway epithelium depends on a highly effective defence provided by airway mucus. Excessive mucus or impaired mucus clearance contributes to the pathogenesis of many common and less common airways diseases. The accumulation of mucus results from some combination of overproduction and decreased clearance and persistent accumulation can lead to infection, inflammation and suitable conditions for microbial growth (Fahy J. V. & Dickey B. F., The New England Journal of Medicine, 363, 2233-2247 (2010)).

Mucus hyper-secretion has been suggested to be an important pathological feature of chronic obstructive pulmonary disease (COPD) (Prescott, E. I. et al., 158, 6456 (1996)), asthma (Aikawa, T. et al., T. Chest, 101, 916 (1992)) and cystic fibrosis (Boucher, R. C. Adv. Drug Deliv. Rev., 54, 1359 (2002)). Substantial epidemiological studies have demonstrated an association between mucus hyper-secretion and increased frequency and duration of respiratory infection, hospitalization, increased levels of morbidity and mortality. It is presently clearly recognised that a hallmark of many airways diseases is an overabundance of goblet cells, referred to as mucus hypersecretory phenotype.

Mucus and the cells that produce it form an integral part of the mucociliary clearance apparatus whose co-ordinated function is considered essential to the protection of the airways from irritant/infectious insult. In healthy airways, secreted mucin is cleared by mucociliary clearance, infrequently assisted by conscious coughing, and does not therefore accumulate. In contrast, plugging of the small airways with mucus together with chronic cough and phlegm production are common manifestations in respiratory diseases.

Small airway plugging with mucus is a major contributing factor to fatal asthma, especially in younger patients (Kuyper, L. M. et al.; Am. J. Med., 115, (2003)), and is associated with goblet cell hyperplasia (Aikawa, T. et al., T. Chest, 101, 916 (1992)). In addition, 20% of asthmatics report chronic cough and phlegm production (Cerveri, S. et al.; Eur Respir J 22: 413-417 (2003)) and highlights the poorly controlled population (de Marco R. et al.; Am J Respir Crit Care Med 175, 32-39 (2007)). These patients are also those with significantly more upper and lower respiratory symptoms (Timonen K. L. et al.; Eur Respir J. March 19, 479-86 (2002)). Importantly, chronic mucus hypersecretion has also been identified as a significant marker of an enhanced decline in lung function in asthmatics (Lange P. et al.; N Engl J Med. 339, 1194-2000 (1998); Ulrik C. S. & Lange P. Am J Respir Crit Care Med. 150, 629-34 (1994)).

Goblet cells, which in healthy subjects are restricted to large airways, have been shown to be increased in numbers in small airways of patients affected by COPD and other respiratory diseases (Hogg J. C. Novartis Foundation Symposium, 234, 4 (2001). Whether goblet cell numbers increase as a consequence of progenitor cell proliferation (hyperplasia), non-mitotic differentiation (metaplasia) or inhibition of necrotic/apoptotic processes or whether one process predominates over the other is still poorly understood.

In the past decades, scientists have been elucidating molecules and pathways that regulate cell fate decisions. Most of these molecules operate in multiple tissues, at different stages of development or disease stage. Notch signaling is an evolutionarily conserved pathway that regulates many cell-fate decisions during development (Fortini, M. E., Dev Cell 16, 633-647 (2009)). Notch signaling in regulating cell fate decisions during development has been studied in many contexts, including in mucociliary tissues. There are 4 Notch receptors in mammalian cells (Notch1-4), which are activated by membrane-bound ligands, members of the Delta and Jagged family, on neighbouring cells. Notch activation leads to a series of cleavage events, culminating in the generation of the Notch intra-cellular domain (NICD), which translocates to the nucleus where it interacts with a transcription factor complex to regulate gene expression. In the epidermis of the *Xenopus* embryo, activation of Notch suppresses the ciliated cell fate, while inhibition of Notch signaling results in an overproduction of ciliated cells (Deblandre, G. A., et al., Development 126, 4715-4728 (1999)). In the developing mouse airway, expression of the NICD results in an overproduction of secretory cells at the expense of ciliated cells (Guseh, J. S., et al. Development 136, 1751-1759 (2009)), while deletion of Pofut1, an O-fucosyl-transferase required for Notch-ligand interactions (Stahl, M., et al., The Journal of biological chemistry 283, 13638-13651 (2008)), or Rbpjk, a core nuclear effector of Notch signalling (Fortini, M. E., Dev Cell 16, 633-647 (2009)), results in an increase in the number of ciliated cells and a near absence of secretory cells (Tsao, P. N., et al., Development 136, 2297-2307 (2009)). A recent study using Notch receptor-specific knockouts suggested that Notch2 is the critical Notch receptor regulating secretory versus ciliated cell fate in the mouse developing airway (Morimoto, M. et al., Development 139, 4365-4373 (2012)). Albeit these recent investigations in the mouse developmental field, the role of Notch2 in the adult lung is not yet understood.

Hence, there is still the need for a greater understanding of the pathways that regulate the function of the human airway epithelium as well as those which define repair and remodelling in both health and disease. Identifying therapeutic targets in these pathways can lead to therapeutics for treating unmet medical needs such as moderate and severe asthma, cystic fibrosis and chronic obstructive pulmonary disease (COPD).

SUMMARY OF THE INVENTION

It has now been found that human Notch2 is required for goblet cell metaplasia in vitro and in vivo. The invention therefore provides for an isolated binding molecule that binds human Notch2 for use in the treatment and/or prevention of a respiratory disease. In one embodiment of this aspect, the respiratory disease is selected from cystic fibrosis (CF), primary ciliary dyskinesia, chronic bronchitis, chronic obstructive pulmonary disease (COPD), asthma or respiratory tract infections. In another embodiment of this aspect, the binding molecule inhibits mucus hyper-secretion or inhibits formation of goblet cells.

The invention also provides for the use of an isolated binding molecule that binds human Notch2 in the manufacture of a medicament for the treatment and/or prevention of a respiratory disease. In one embodiment of this aspect, the respiratory disease is selected from cystic fibrosis (CF), primary ciliary dyskinesia, chronic bronchitis, chronic obstructive pulmonary disease (COPD), asthma or respiratory tract infections. In another embodiment of this aspect, the binding molecule inhibits mucus hyper-secretion or inhibits formation of goblet cells.

The invention also provides for a method of treatment and/or prevention of respiratory disease comprising administering an isolated binding molecule that binds human Notch-2 to a subject in need thereof. In one embodiment of this aspect, the respiratory disease is selected from cystic fibrosis (CF), primary ciliary dyskinesia, chronic bronchitis, chronic obstructive pulmonary disease (COPD), asthma or respiratory tract infections. In another embodiment of this aspect, the binding molecule inhibits mucus hyper-secretion or inhibits formation of goblet cells.

In some embodiments of these aspects, the isolated binding molecule binds human Notch2 extracellular domain or a soluble human Notch2 fragment. In some other embodiments the isolated binding molecule comprises an antigen-binding portion of an antibody. In some other embodiments of these aspects the isolated binding molecule is an antagonist antibody or a fragment thereof, preferably selected from antibody D3, antibody 59R5 or functional fragments thereof. In some embodiments of these aspects the isolated binding molecule is a fibronectin molecule. In some other embodiments the isolated binding molecule does not cross-react with Notch1, Notch3 or Notch4.

The invention also provides the isolated binding molecule, the use or the method according to any one of the preceding claims, wherein the binding molecule is formulated with a pharmaceutical acceptable carrier.

DETAILED DESCRIPTION OF THE INVENTION

Definitions

Figure 1:
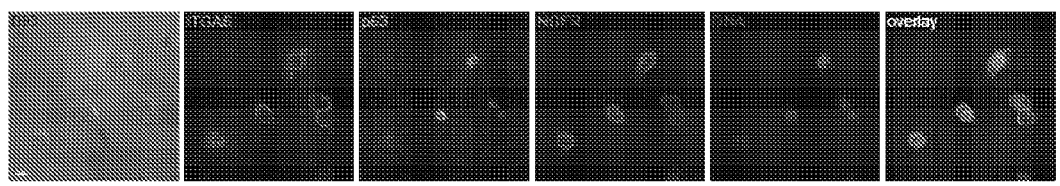
FIG. 1: Human airway basal cells form 'bronchospheres' in 3D culture. (a) Human bronchial epithelial cells (HBECs) were grown in chambered slides and stained for integrin α6 (ITGA6, green), p63 (orange), nerve growth factor receptor (NGFR, red), and DNA (blue). All of the HBECs are positive for the airway basal cell markers ITGA6, p63, and NGFR. The differential interference contrast (DIC) image is shown on the left, and the overlay is on the right. Scalebar=10 µm. (b) Phase contrast image of day 14 bronchospheres. Scalebar=100 µm. (c) Quantitative PCR analysis of goblet (MUC5AC, MUC5B, FOXA3), ciliated (FOXJ1, DNAI2), and basal cell markers (p63, ITGA6) expressed by HBECs grown on plastic or after 14 days of growth in 3D. Shown is the average+/−SEM of at least 4 independent donors. (d) Day 14 bronchospheres were fixed and stained for DNA (blue), and markers of basal cells (p63, red), ciliated cells (acetylated α-Tubulin, orange), and goblet cells (MUC5AC, green). Scalebar=50 µm. (e) Human airway basal cells labeled with Oregon Green 488 Carboxylic Acid Diacetate (carboxy-DFFDA; Invitrogen®) mixed with an equal amount of unlabeled cells, plated in 3D at different seeding densities and imaged after 3 days in culture. At seeding densities of 75 cells per well and lower, structures are clonal, exclusively containing either labeled or unlabelled cells. Scalebar=50 µm. (f) Day 20 bronchospheres derived from human airway basal cells plated at a clonal density (75 cells/well) stained for DNA (blue), and markers of basal cells (p63, red), ciliated cells (acetylated α-Tubulin, orange), and goblet cells (MUC5AC, green). Scalebar=50 µm.
Figure 1:
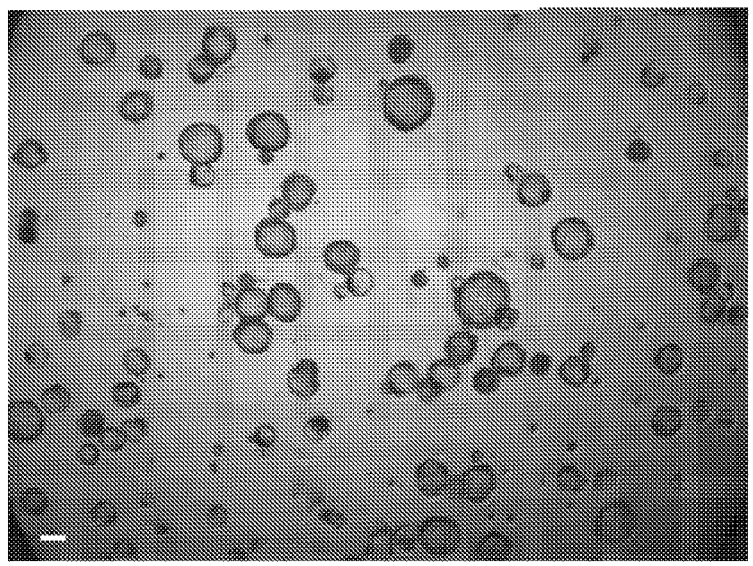
Figure 1:
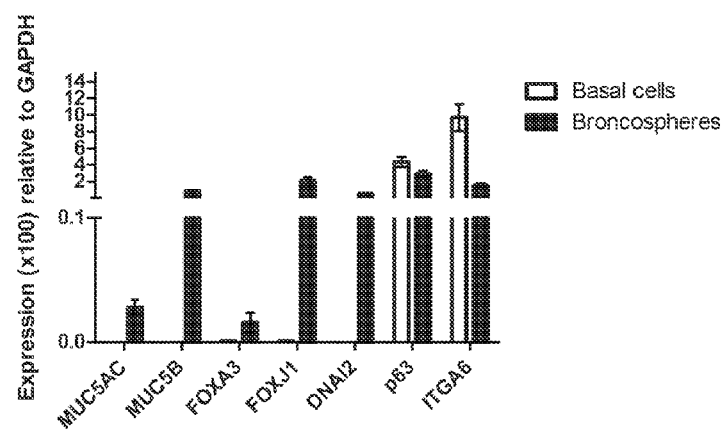
Figure 1:
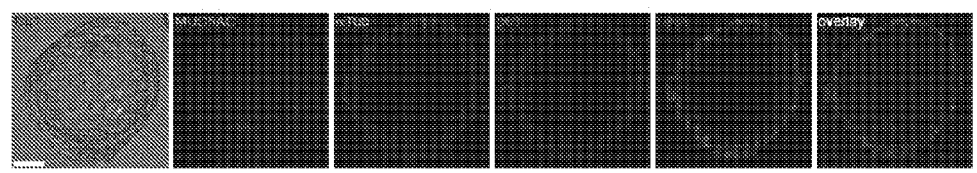
Figure 1:
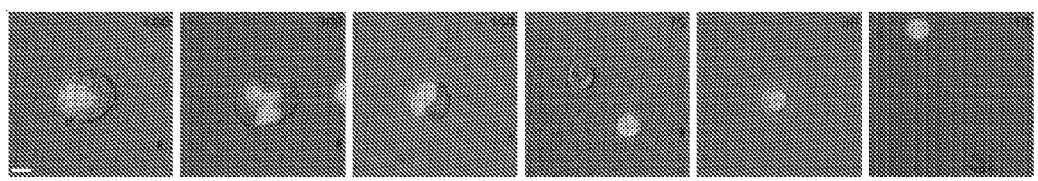
Figure 1:
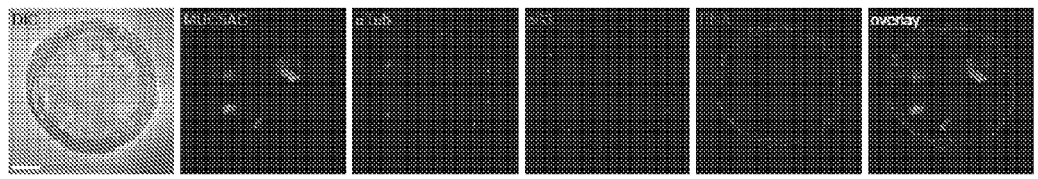

For purposes of interpreting this specification, the following definitions will apply and whenever appropriate, terms used in the singular will also include the plural and vice versa. Additional definitions are set forth throughout the detailed description.

The term "Notch2" refers to human Notch2, unless it is specified otherwise, having amino acid sequence for example as defined in Q04721.

The term "Notch2" is synonym to Notch-2, Notch_2, Notch-2 receptor, Neurogenic locus notch homolog protein 2, Notch 2, Notch (*Drosophila*) homolog 2, Notch homolog 2 (*Drosophila*), or hN2.

The term "binding molecule" as used herein means any protein or peptide that binds specifically to human Notch2. "Binding molecule" includes, but it is not limited to, antibodies and fragments thereof, such as immunologically functional fragments. The term "immunologically functional fragment" of an antibody or immunoglobulin chain as used herein is a species of binding protein comprising a portion, regardless of how that portion is obtained or synthesized of an antibody (an antigen-binding portion) that lacks at least some of the amino acids present in a full-length chain but which is still capable of specifically binding Notch2. Such fragments are biologically active in that they bind Notch2.

The term "antibody" refers to an intact immunoglobulin or a functional fragment thereof. As used herein, the term "antibody" means a polypeptide comprising a framework region from an immunoglobulin gene or fragments thereof that specifically binds and recognizes an epitope, e.g. an epitope found on human Notch2. Naturally occurring antibodies typically comprise a tetramer which is usually composed of at least two heavy (H) chains and at least two light (L) chains. Each heavy chain is comprised of a heavy chain variable region (abbreviated herein as VH) and a heavy chain constant region, usually comprised of three domains (CH1, CH2 ad CH3). Heavy chains can be of any isotype, including IgG (IgG1, IgG2, IgG3 and IgG4 subtypes), IgA (IgA1 and IgA2 subtypes), IgM and IgE. Each light chain is comprised of a light chain variable region (abbreviated herein as VL) and a light chain constant region (CL). Light chain includes kappa chains and lambda chains. The heavy and light chain variable region is typically responsible for antigen recognition, whilst the heavy and light chain constant region may mediate the binding of the immunoglobulin to host tissues or factors, including various cells of the immune system (e.g., effector cells) and the first component (C1q) of the classical complement system. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen.

The term "antibody" includes whole antibodies (such as monoclonal, chimeric, humanised and human antibodies), including single-chain whole antibodies, and antigen-binding fragments thereof. The term "antibody" includes antigen-binding antibody fragments, including single-chain antibodies, which can comprise the variable regions alone, or in combination, with all or part of the following polypeptide elements: hinge region, CH1, CH2, and CH3 domains of an antibody molecule. Also included within the definition are any combinations of variable regions and hinge region, CH1, CH2, and CH3 domains. Antibody fragments include, e.g., but are not limited to, Fab, Fab' and F(ab')2, Fd, single-chain Fvs (scFv), single-chain antibodies, disulphide-linked Fvs (sdFv) and fragments comprising either a VL or VH domain. Examples include: (i) a Fab fragment, a monovalent fragment consisting of the VL, VH, CL and CH1 domains; (ii) a F(ab')2 fragment, a bivalent fragment comprising two Fab fragments linked by a disulphide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature 341, 544-546 (1989); Muyldermans et al., TIBS 24, 230-235 (2001)), which consists of a VH domain; and (vi) an isolated complementarity determining region (CDR). The term "antibody" includes single domain antibodies, maxibodies, minibodies, intrabodies, diabodies, triabodies, tetrabodies, v-NAR and bis-scFv (Hollinger & Hudson, Nature Biotechnology, 23, 9, 1126-1136 (2005)). Antigen binding portions can be incorporated into single chain molecules comprising a pair of tandem Fv segments (VH-CH1-VH-CH1) which, together with complementary light chain polypeptides, form a pair of antigen binding regions (Zapata et al., Protein Eng. 8, 1057-1062 (1995); and U.S. Pat. No. 5,641,870).

The term "antigen-binding portion" of an antibody as used herein, refers to full length or one or more fragments of an antibody that retain the ability to specifically bind to human Notch2. It has been shown that the antigen-binding function of an antibody can be performed by fragments of a full-length antibody. Examples of binding fragments encompassed within the term "antigen-binding portion" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature; 341:544-546), which consists of a VH domain; and an isolated complementarity determining region (CDR).

The term "isolated" means throughout this specification, that the binding molecule, the immunoglobulin or antibody, as the case may be, exists in a physical milieu distinct from that in which it may occur in nature.

An isolated antibody that binds human Notch2 may, however, have cross-reactivity to other antigens, such as Notch2 from other species (e.g. cynomolgus monkey, mouse or *Drosophila*). Moreover, an isolated antibody may be substantially free of other cellular material and/or chemicals.

As used herein, a binding molecule that "binds to human Notch2" is intended to refer to a binding molecule that binds to Notch2 with a $K_D$ of a $1\times10^{-6}$ M or less, or $1\times10^{-7}$ M or less, or $1\times10^{-8}$ M or less, or $1\times10^{-9}$ M or less, $1\times10^{-10}$ M or less.

As used herein, the term "subject" includes any human or non-human animal.

The term "non-human animal" includes all vertebrates, e.g., mammals and non-mammals, such as non-human primates, sheep, dogs, cats, horses, cows, chickens, amphibians, reptiles, etc.

A "signal transduction pathway" or "signaling activity" or "downstream pathway" refers to a biochemical causal relationship generally initiated by a protein-protein interaction such as binding of a growth factor to a receptor, resulting in transmission of a signal from one portion of a cell to another portion of the cell. For example, the transmission may involve specific phosphorylation of one or more tyrosine, serine, or threonine residues on one or more proteins in a series of reactions causing signal transduction. In general, penultimate processes typically include nuclear events, resulting in a change in gene expression or cytoplasmic events, resulting in a change of cell function.

The term "antagonist antibody or a fragment thereof" or "neutralizing antibody or a fragment thereof" means an antibody or fragment thereof which binds Notch2 and inhibit Notch2 biological activity and/or downstream pathway(s) regulated by Notch2 signaling. An anti-Notch2 antagonist antibody encompasses antibodies that block, nullify, antagonize, suppress, decrease or reduce (including significantly), in any meaningful degree, Notch2 biological activity, including downstream pathways regulated by Notch2 signaling, or elicitation of a cellular response to Notch2.

The term "epitope" includes any protein determinant capable of specific binding to an immunoglobulin or otherwise interacting with a molecule. Epitopic determinants generally consist of chemically active surface groupings of molecules such as amino acids or carbohydrate or sugar side chains and can have specific three-dimensional structural characteristics, as well as specific charge characteristics. An epitope may be "linear" or "conformational." Within the present specification, the term "epitope" is used interchangeably for both conformational epitopes and linear epitopes. A conformational epitope is composed of discontinuous sections of the antigen's amino acid sequence, whilst a linear epitope is formed by a continuous sequence of amino acids from the antigen.

The term "treat", "treating", "treatment", "prevent", "preventing" or "prevention" includes therapeutic treatments, prophylactic treatments and applications in which one reduces the risk that a subject will develop a disorder or other risk factor. Treatment and/or prevention do not require the complete curing of a disorder and encompasses the reduction of the symptoms or underlying risk factors or at least a slowing down of the progression of the disease.

The term "comprising" means "including" as well as "consisting" e.g., a composition "comprising" X may consist exclusively of X or may include something additional e.g., X+Y.

The term "about" in relation to a numerical value x means, for example, x+10%. References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of Current Protocols in Molecular Biology (F. M. Ausubel et al., eds., 1987) Supplement 30. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in Smith & Waterman (1981) Adv. Appl. Math. 2: 482-489

Inflammatory Cytokine-Driven Goblet Cell Metaplasia and Mucus Hyper-Secretion

A number of inflammatory cytokines and growth factors have been reported to increase the expression of MUC5AC in airway epithelial cells (Chen, Y., et al., The Journal of biological chemistry 278, 17036-17043 (2003); Fujisawa, T., et al., J Immunol 183, 6236-6243 (2009); Gray, T., et al., American journal of physiology. Lung cellular and molecular physiology 286, L320-330 (2004) and Kim, Y. D., et al., Molecular pharmacology 62, 1112-1118 (2002)), a mucin that is up-regulated in a number of airway diseases, including asthma and COPD (Fahy, J. V. & Dickey, B. F, The New England journal of medicine 363, 2233-2247 (2010)). However, the mechanism by which soluble factors lead to increased MUC5AC levels is not fully understood.

IL-13 has been shown to be a key mediator of allergic asthma in numerous pre-clinical and clinical studies. It is known that polymorphisms in both IL-13 and the IL-4 receptor (a component of the IL-13 receptor complex) are associated with asthma susceptibility and that IL-13 induced pathways are linked to airway responses in asthma (reviewed in: Ingram & Kraft, 2012; J All Clin Imm 130(4): 829; Wills-Karp, M., Immunological reviews 202, 175-190 (2004)). Amongst the reported effects of IL-13 that are of relevance to asthma, several groups have demonstrated that IL-13 acts directly on the epithelium to drive a goblet cell metaplasia phenotype by increasing the number of goblet cells in vitro and in vivo by altering the airway epithelial cell fate (Atherton, H. C. et al., American journal of physiology. Lung cellular and molecular physiology 285, L730-739 (2003); Kuperman, D. A., et al., Nature medicine 8, 885-889 (2002) and Laoukili, J., et al., The Journal of clinical investigation 108, 1817-1824 (2001)).

IL-17A has been reported to play a critical role in allergic asthma (Souwer, Y. et al, Current opinion in immunology 22, 821-826 (2010)). IL-17A protein levels are increased in airway lavage, biopsy samples, sputum and blood of asthmatic patients (reviewed in: Silverpil & Linden, 2012; Exp Rev Respir Med 6(2):173). IL-17A is a cytokine that is secreted by Th17 cells, and has been shown to stimulate mucin gene expression in cultured airway epithelial cells (Chen, Y., et al., The Journal of biological chemistry 278, 17036-17043 (2003)), and enhance airway smooth muscle contraction in vivo (Kudo, M., et al., Nature medicine 18, 547-554 (2012)).

The balance and distribution of epithelial cell types is required to maintain tissue homeostasis and perturbations of this balance are hallmarks of human respiratory diseases, including goblet cell metaplasia and enhanced mucus secretion in asthma and COPD. In the conducting airway, basal cells act as progenitors for both secretory and ciliated cells. Studying the development and function of these varied airway cell types and to identify mechanism regulating cell fate decisions in the airways has been advanced in the recent years by air-interface (ALI) cultures of primary epithelia (Gray, T. E. et al, American journal of respiratory cell and molecular biology 14, 104-112 (1996)). In these systems, cells are cultured on a permeable support to confluency, at which time media is removed from the apical side resulting in polarization and differentiation of the epithelium. With respect to the human proximal airways, ALI cultures of primary tracheo-bronchial cells replicate the architecture of the native epithelium, together with ion transport function and an intact mucociliary clearance system. Although these ALI systems are now largely routine, the polarization and differentiation of the epithelium is dependent on the use of the permeable insert that can limit their utility in terms of throughput and availability of primary cells.

A proposed alternative to the use of a permeable insert to drive epithelial polarization is to culture in 3D extracellular matrix (ECM). Three-dimensional culture models utilizing cell lines derived from several epithelial tissues, including kidney (MDCK), intestine (Caco-2) and mammary gland (MCF-10A) have been previously described (Debnath, J. et al., Methods 30, 256-268 (2003); Jaffe, A. B. et al., J Cell Biol 183, 625-633 (2008); Elia, N. & Lippincott-Schwartz, J., Current protocols in cell biology/editorial board, Chapter 4, Unit 4 22 (2009)). Recently, the formation of "tracheospheres" from either Krt5$^+$ murine basal cells or ITGA6$^+$ NGFR$^+$ human basal cells in 3D Matrigel-based culture has been described. Tracheospheres contained a central lumen surrounded by ciliated cells, but lacked detectable MUC5AC$^+$ secretory cells (Rock, J. R., et al. Proceedings of the National Academy of Sciences of the United States of America 106, 12771-12775 (2009)). It has also been reported the formation of polarized 3D structures in Matrigel that were derived from surface epithelial HBE cells. These structures that were cultured on 4 chamber slides were termed "glandular acinar" cells based upon the expression of MUC5B (Wu, X. et al., American journal of respiratory cell and molecular biology 44, 914-921 (2011)). While each of these systems recapitulates some aspects of the architecture of the conducting airway, neither capture the full diversity of cell types found in this region of the respiratory tract.

Herein we utilize a novel culture model of airway epithelial morphogenesis, which produces several features of the conducting airway, including a pseudostratified epithelium containing basal cell progenitors, mucus-secreting goblet cells, and ciliated cells, surrounding a single central lumen. We used this system to screen a panel of secreted proteins, and found that several cytokines were able to alter the fate of an airway basal cell, resulting in reduced ciliated cell differentiation and increased goblet cell differentiation.

Using this novel method for the 3D culture of primary human bronchial epithelial (HBE) cells, bronchospheres, (see examples section) we have demonstrated that bronchospheres derive from pluripotent p63$^+$NGFR$^+$ITGA6$^+$ airway basal cells, a progenitor cell for the human conducting epithelium, and display key features of the conducting airway epithelium, including a pseudostratified morphology, functional cilia, and mucin-secreting goblet cells. Developing bronchospheres respond to IL-13 with an increase in the expression of markers of goblet cells and a decline in ciliated cell number. We have conducted a focused screen for secreted factors that influence bronchosphere development, and found inflammatory cytokines that can bias basal cell differentiation towards a goblet cell fate thereby altering the composition of the airway epithelium to produce the goblet cell metaplasia described in many respiratory diseases.

This finding has several implications for the treatment of airway diseases. First, it provides a rationale for the development of cytokine-specific therapies and stratifying patients based on either levels of a particular cytokine or a biomarker indicating activation of a pathway downstream of a particular cytokine. Second, it suggests that treatments designed to inhibit the production or secretion of mucus from goblet cells through attenuation of a single mediator may not be sufficient, since they may not restore the appropriate numbers of ciliated cells required for adequate mucociliary clearance. Additionally, although the cytokines we found to influence basal cell fate activate distinct signaling pathways, their similar effect on a cellular process, progenitor cell fate, suggested that there may be a common drugable node that would have therapeutic benefit for patients with a wide range of underlying causes.

We found that human Notch2 acts as a common node downstream of each of these new mediators of goblet cell metaplasia. Notch2, one of the four Notch receptors found in human (Notch1, 2, 3 and 4) consists of a heterodimeric receptor formed by a N-terminus fragment (NEC) that contains most of the extracellular region and a C-terminus fragment ($N^{TM}$), which is cleaved N-terminally to the transmembrane domain. These two fragments are tethered together on the plasma membrane (Blaumueller C. M. et al; Cell 90, 281-291 (1997)). Herein it is shown that antibodies inhibiting human Notch2, but not other Notch receptor family members such as Notch1 and Notch3, inhibit IL-13-driven goblet cell metaplasia in vitro and in vivo. Moreover, anti-Notch2 antibodies prevented the changes in basal cell fate driven by multiple cytokines in 3D bronchosphere system. Collectively, our data supports binding molecules that binds human Notch2 for use in the treatment of respiratory diseases such as cystic fibrosis (CF), primary ciliary dyskinesia, chronic bronchitis, chronic obstructive pulmonary disease (COPD), asthma or respiratory tract infections, characterized by excessive goblet cell formation and mucus hyper-secretion, regardless of the disease stimulus.

Binding Molecules and Methods of Use

Various (enumerated) embodiments of the invention are described herein. It will be recognised that features specified in each embodiment may be combined with other specified features to provide further embodiments of the present invention.

The isolated binding molecule, for use in the treatment and/or prevention of respiratory diseases, binds human Notch2.

Embodiment 1

The isolated binding molecule that binds human Notch2 for use in the treatment and/or prevention of respiratory diseases, wherein the binding molecule inhibits goblet cell formation and/or mucus hyper-secretion.

Embodiment 2

The isolated binding molecule that binds human Notch2 for use in the treatment and/or prevention of respiratory diseases according to embodiment 1, wherein the binding molecule does not cross-react with an antigen other than Notch2, for example the binding molecule does not cross-react with Notch1 or Notch3.

Embodiment 3

The isolated binding molecule that binds human Notch2 for use in the treatment and/or prevention of respiratory diseases according to embodiment 1 or 2, wherein the respiratory disease is selected from cystic fibrosis (CF), primary ciliary dyskinesia, chronic bronchitis, chronic obstructive pulmonary disease (COPD), asthma or respiratory tract infections.

Embodiment 4

The isolated binding molecule that binds human Notch2 for use in the treatment and/or prevention of respiratory diseases according to any one of embodiments 1 to 3, wherein the respiratory disease is an IL-13-mediated respiratory disease.

Embodiment 5

The isolated binding molecule that binds human Notch2 for use in the treatment and/or prevention of respiratory diseases according to any one of embodiments 1 to 3, wherein the respiratory disease is an IL-17A-mediated respiratory disease.

Embodiment 6

The isolated binding molecule that binds human Notch2 for use in the treatment and/or prevention of respiratory diseases according to any one of embodiments 1 to 5, wherein the isolated binding molecule comprises an antigen-binding portion of an antibody or the isolated binding molecule is an antibody or a fragment thereof, preferably a human antibody or fragment thereof.

Embodiment 7

The isolated binding molecule that binds human Notch2 for use in the treatment and/or prevention of respiratory diseases according to any one of embodiments 1 to 6, wherein the binding molecule is an antagonist antibody (or a fragment thereof) or a neutralizing antibody (or a fragment thereof) that binds human Notch2.

Embodiment 8

The isolated binding molecule that binds human Notch2 for use in the treatment and/or prevention of respiratory diseases according to any one of embodiments 1 to 7, wherein the binding molecule is an antagonist antibody (or a fragment thereof) or a neutralizing antibody (or a fragment thereof), wherein when the antibody or fragment thereof, once bound to human Notch2, inhibits Notch2 biological activity and/or downstream pathway(s) mediated by Notch2 signaling.

Embodiment 9

The isolated binding molecule that binds human Notch2 for use in the treatment and/or prevention of respiratory diseases according to embodiment 8, wherein the binding molecule inhibits goblet cell formation and/or inhibits mucus hyper-secretion.

Embodiment 10

The isolated binding molecule that binds human Notch2 for use in the treatment and/or prevention of respiratory diseases according to any one of embodiments 1 to 9, wherein the binding molecule is selected from antibody D3, antibody 59R5 or functional fragments thereof.

Embodiment 11

The isolated binding molecule that binds human Notch2 for use in the treatment and/or prevention of respiratory diseases according to embodiment 10, wherein the binding molecule binds human Notch2 extracellular domain and is selected from antibody D3, antibody 59R5 or functional fragments thereof.

Embodiment 12

The isolated binding molecule that binds human Notch2 for use in the treatment and/or prevention of respiratory diseases according to embodiment 10 or 11, wherein the binding molecule is selected from antibody D3, antibody 59R5 or functional fragments thereof and the respiratory disease is selected from cystic fibrosis (CF), primary ciliary dyskinesia, chronic bronchitis, chronic obstructive pulmonary disease (COPD), asthma or respiratory tract infections.

Embodiment 13

The isolated binding molecule that binds human Notch2 for use in the treatment and/or prevention of respiratory diseases according to any one of embodiments 10 to 12, wherein the antibody inhibits goblet cell formation and/or inhibits mucus hyper-secretion.

Embodiment 14

The isolated binding molecule that binds human Notch2 for use in the treatment and/or prevention of respiratory diseases according to any one of embodiments 1 to 13, wherein the binding molecule is selected from an antibody that binds the non-ligand binding region of Notch2 extracellular domain and the respiratory disease is selected from cystic fibrosis (CF), primary ciliary dyskinesia, chronic bronchitis, chronic obstructive pulmonary disease (COPD), asthma or respiratory tract infections. Preferably, the antibody inhibits goblet cell formation and/or inhibits mucus hyper-secretion.

Embodiment 15

The isolated binding molecule that binds human Notch2 for use in the treatment and/or prevention of respiratory diseases according to any one of embodiments 1 to 13, wherein the binding molecule is selected from an antibody that binds the negative regulatory region (NRR) of Notch2 extracellular domain and the respiratory disease is selected from cystic fibrosis (CF), primary ciliary dyskinesia, chronic bronchitis, chronic obstructive pulmonary disease (COPD), asthma or respiratory tract infections. Preferably, this antibody inhibits goblet cell formation and/or inhibits mucus hyper-secretion.

Embodiment 16

The isolated binding molecule that binds human Notch2 for use in the treatment and/or prevention of respiratory diseases according to any one of embodiments 1 to 13, wherein the binding molecule is selected from an antibody that binds the antibody EGF repeat 10 of Notch2, preferably sequence HKGAL within EGF repeat 10 of Notch2 and the respiratory disease is selected from cystic fibrosis (CF), primary ciliary dyskinesia, chronic bronchitis, chronic obstructive pulmonary disease (COPD), asthma or respiratory tract infections. Preferably, the antibody inhibits goblet cell formation and/or inhibits mucus hyper-secretion.

Embodiment 17

The isolated binding molecule that binds human Notch2 for use in the treatment and/or prevention of respiratory diseases according to any one of embodiments 1 to 13, wherein the binding molecule is selected from an antibody that competes with antibody 59R5 or antibody D3 for binding Notch2 and the respiratory disease is selected from cystic fibrosis (CF), primary ciliary dyskinesia, chronic bronchitis, chronic obstructive pulmonary disease (COPD), asthma or respiratory tract infections. Preferably, the antibody inhibits goblet cell formation and/or inhibits mucus hyper-secretion.

Examples of isolated antibodies which bind Notch2 include, but are not limited to, the antibodies illustrated by sequence in Table 1 below.

TABLE 1

List of anti-Notch2 antibodies, their amino acid sequences and identities.

| SEQ. I.D. NO: | SEQUENCE | Identity |
|---|---|---|
| 1 | QVQLVESGGGLVQPGGSLRLSCAASGFTFSSYWIHWVRQAPGKGLEWVARINPP NRSNQYADSVKGRFTISADTSKNTAYLQMNSLRAEDTAVYYCARGSGFRWVMDY WGQGTLVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKR VEPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEYKCK VSNKALPAPIEKTISKAKGQPREPQVYTLPPSREEMTKNQVSLTCLVKGFYPSD IAVEWESNGQPENNYKTTPPVLDSDGSFFLYSKLTVDKSRWQQGNVFSCSVMHE ALHNHYTQKSLSLSPGK | Heavy chain A2 |
| 2 | DIQMTQSPSSLSASVGDRVTITCRASQDVSTAVAWYQQKPDGTVKLLIYSASFL YSGVPSRFSGSGSGTDFTLTISSLQPEDFATYYCQQFYTTPSTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC | Light chain A2 |
| 3 | QVQLVESGGGLVQPGGSLRLSCAAGYTFSSYGMSWVRQAPGKGLEWVSYIYPYS GATYYADSVKGRFTISADTSKNTAYLQMNSLRAEDTAVYYCARHSGYYRISSAM DVWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KRVEPKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK | Heavy chain D3 |
| 4 | DIQMTQSPSSLSASVGDRVTITCRASQNIKRFLAWYQQKPGKAPKLLIYGASTR ESGVPSRFSGSGSGTDFTLTISSLQPEDFATYYCQQYYRSPHTFGQGTKVEIKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC | Light chain D3 |
| 5 | EVQLVESGGGLVQPGGSLRLSCAASGFTFSSSGMSWVRQAPGKGLEWVSVIASS GSNTYYADSVKGRFTISRDNSKNTLYLQMNSLRAEDTAVYYCARSIFYTTWGQG TLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKRVEPK SCDKTHTCPPCPAPELLGGPSVFLFPPKPKDTLMISRTPEVTCVVVDVSHEDPE VKFNWYVDGVEVHNAKTKPREEQYNSTYRVVSVLTVLHQDWLNGKEYKCKVSNK ALPAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALHN HYTQKSLSLSPGK | Heavy chain 59R5 |
| 6 | DIVLTQSPATLSLSPGERATLSCRASQSVRSNYLAWYQQKPGQAPRLLIYGASS RATGVPARFSGSGSGTDFTLTISSLEPEDFAVYYCQQYSNFPITFGQGTKVEIK RTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC | Light chain 59R5 |

TABLE 1-continued

List of anti-Notch2 antibodies, their amino acid sequences and identities.

| SEQ. I.D. NO: | SEQUENCE | Identity |
|---|---|---|
| 7 | EVQLVESGGGLVQPGGSLKLSCAASGFTFSHYYMSWVRQTPEKRLEWVAYISNG GGRTDYPDSVKGRFTISRDNAKNTLHLQMSSLKSEDTAMYYCTRLDYFGGSPYF DYWGQGTTLTVSSAKTTPPSVYPLAPGSAAQTNSMVTLGCLVKGYFPEPVTVTW NSGSLSSGVHTFPAVLQSDLYTLSSSVTVPSSTWPSETVTCNVAHPASSTKVDK KIVPRDCGCKPCICTVPEVSSVFIFPPKPKDVLTITLTPKVTCVVVDISKDDPE VQFSWFVDDVEVHTAQTQPREEQFNSTFRSVSELPIMHQDWLNGKEFKCRVNSA AFPAPIEKTISKTKGRPKAPQVYTIPPPKEQMAKDKVSLTCMITDFFPEDITVE WQWNGQPAENYKNTQPIMDTDGSYFVYSKLNVQKSNWEAGNTFTCSVLHEGLHN HHTEKSLSHSPGK | Heavy chain A4 |
| 8 | EIVLTQSPAITAASLGQKVTITCSASSSVSYMHWYQQKSGTSPKPWIYEISKLA SGVPPRFSGSGSGTSYSLTISSMEAEDAAIYYCQQWNYPLITFGSGTKLEIKRA DAAPTVSIFPPSSEQLTSGGASVVCFLNNFYPKDINVKWKIDGSERQNGVLNSW TDQDSKDSTYSMSSTLTLTKDEYERHNSYTCEATHKTSTSPIVKSFNRNEC | Light chain A4 |
| 9 | EVQLVESGGGLVQPGGSLRLSCAAGYTFSSYGMSWVRQAPGKGLEWVSYIYPYSGATYY ADSVKGRFTISADTSKNTAYLQMNSLRAEDTAVYYCARHSGYYRISSAMDVWGQGTLVT VSSASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPCPAP ELLGGPSVFLFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDSDGSFFLYSK LTVDKSRWQQGNVFSCSVMHEALHNHYTQKSLSLSPGK | Q→E Heavy chain D3 |

Embodiment 18

The isolated binding molecule that binds human Notch2 for use in the treatment and/or prevention of respiratory diseases according to embodiment 1, wherein the binding molecule is selected from an isolated antibody comprising a heavy chain comprising SEQ ID NO: 1 and a light chain comprising SEQ ID NO: 2 or a heavy chain comprising SEQ ID NO: 3 or SEQ ID NO: 9 and a light chain comprising SEQ ID NO: 4 or a heavy chain comprising SEQ ID NO: 5 and a light chain comprising SEQ ID NO:6 or a heavy chain comprising SEQ ID NO: 7 and a light chain comprising SEQ ID NO:8.

Embodiment 19

The isolated binding molecule that binds human Notch2 for use in the treatment and/or prevention of respiratory diseases according to embodiment 1, wherein the binding molecule is selected from an isolated antibody comprising a heavy chain comprising SEQ ID NO: 3 or SEQ ID NO: 9 and a light chain comprising SEQ ID NO: 4.

Embodiment 20

The isolated binding molecule that binds human Notch2 for use in the treatment and/or prevention of respiratory diseases according to embodiment 1, wherein the binding molecule is selected from an isolated antibody comprising a heavy chain comprising SEQ ID NO: 5 and a light chain comprising SEQ ID NO:6.

Embodiment 21

The isolated binding molecule that binds human Notch2 for use in the treatment and/or prevention of respiratory diseases according to embodiment 1, wherein the binding molecule is selected from an isolated antibody comprising a heavy chain comprising SEQ ID NO: 3 or SEQ ID NO: 9 and a light chain comprising SEQ ID NO: 4 wherein the respiratory disease is selected from cystic fibrosis (CF), primary ciliary dyskinesia, chronic bronchitis, chronic obstructive pulmonary disease (COPD), asthma or respiratory tract infections. Preferably this antibody inhibits goblet cell formation and/or inhibits mucus hyper-secretion.

Embodiment 22

The isolated binding molecule that binds human Notch2 for use in the treatment and/or prevention of respiratory diseases according to embodiment 1, wherein the binding molecule is selected from an isolated antibody comprising a heavy chain comprising SEQ ID NO: 5 and a light chain comprising SEQ ID NO: 6 wherein the respiratory disease is selected from cystic fibrosis (CF), primary ciliary dyskinesia, chronic bronchitis, chronic obstructive pulmonary disease (COPD), asthma or respiratory tract infections. Preferably this antibody inhibits goblet cell formation and/or inhibits mucus hyper-secretion.

Embodiment 23

The isolated binding molecule that binds human Notch2 for use in the treatment and/or prevention of respiratory diseases according to embodiment 1, wherein the binding molecule is selected from an isolated antibody comprising a heavy chain comprising SEQ ID NO: 5 and a light chain comprising SEQ ID NO: 6 wherein the respiratory disease is cystic fibrosis (CF). Preferably this antibody inhibits goblet cell formation and/or inhibits mucus hyper-secretion.

Embodiment 24

The isolated binding molecule that binds human Notch2 for use in the treatment and/or prevention of respiratory diseases according to embodiment 1, wherein the binding molecule is selected from an isolated antibody comprising a heavy chain comprising SEQ ID NO: 5 and a light chain comprising SEQ ID NO: 6 wherein the respiratory disease is chronic obstructive pulmonary disease (COPD). Preferably this antibody inhibits goblet cell formation and/or inhibits mucus hyper-secretion.

Embodiment 23

The isolated binding molecule that binds human Notch2 for use in the treatment and/or prevention of respiratory diseases according to embodiment 1, wherein the binding molecule is selected from an isolated antibody comprising a heavy chain comprising SEQ ID NO: 5 and a light chain comprising SEQ ID NO: 6 wherein the respiratory disease is asthma. Preferably this antibody inhibits goblet cell formation and/or inhibits mucus hyper-secretion.

Embodiment 24

The isolated binding molecule that binds human Notch2 for use in the treatment and/or prevention of respiratory diseases according to embodiment 1, wherein the binding molecule is selected from an isolated antibody comprising a heavy chain comprising SEQ ID NO: 5 and a light chain comprising SEQ ID NO:6 wherein the respiratory disease is chronic bronchitis. Preferably this antibody inhibits goblet cell formation and/or inhibits mucus hyper-secretion.

Embodiment 25

The isolated binding molecule that binds human Notch2 for use in the treatment and/or prevention of respiratory diseases according to embodiment 1, wherein the binding molecule is selected from an isolated antibody comprising a heavy chain comprising SEQ ID NO: 5 and a light chain comprising SEQ ID NO: 6 wherein the respiratory disease is a respiratory tract infection. Preferably this antibody inhibits goblet cell formation and/or inhibits mucus hyper-secretion.

Embodiment 26

The isolated binding molecule that binds human Notch2 for use in the treatment and/or prevention of respiratory diseases according to embodiment 1, wherein the binding molecule is selected from an isolated antibody comprising a heavy chain comprising SEQ ID NO: 5 and a light chain comprising SEQ ID NO: 6 wherein the respiratory disease is primary ciliary dyskinesia. Preferably this antibody inhibits goblet cell formation and/or inhibits mucus hyper-secretion.

Other examples of isolated antibodies that binds Notch2 extracellular domain are exemplified in WO2007145840, WO2008091641, WO2010005566 and WO2010039832, which references are incorporated herein.

Embodiment 27

The isolated binding molecule that binds human Notch2 for use in the treatment and/or prevention of respiratory diseases according to any one of embodiments 1 to 5, wherein the isolated binding molecule is selected from a fibronectin molecule, an adnectin, a DARPin, an avimer, an affibody, an anticalin, an affilin, a protein epitope mimetic or combinations thereof.

Embodiment 28

The isolated binding molecule that binds human Notch2 for use in the treatment and/or prevention of respiratory diseases according to embodiment 27, wherein the isolated binding molecule is a fibronectin molecule.

Embodiment 29

The isolated binding molecule that binds human Notch2 for use in the treatment and/or prevention of respiratory diseases according to embodiment 28, wherein the isolated binding molecule is a fibronectin molecule and wherein the respiratory disease is selected from cystic fibrosis (CF), primary ciliary dyskinesia, chronic bronchitis, chronic obstructive pulmonary disease (COPD), asthma or respiratory tract infections.

Embodiment 30

The isolated binding molecule that binds human Notch2 for use in the treatment and/or prevention of respiratory diseases according to embodiment 29, wherein the isolated binding molecule is a fibronectin molecule and wherein the respiratory disease is selected from cystic fibrosis (CF), primary ciliary dyskinesia, chronic bronchitis, chronic obstructive pulmonary disease (COPD), asthma or respiratory tract infections and wherein the fibronectin molecule inhibits goblet cell formation and/or inhibits mucus hyper-secretion.

Embodiment 31

A method of culturing a three-dimensional pseudostratified mucociliary epithelium by (a) plating cells on a Matrigel-coated surface and (b) treating the cells with a differentiation media, wherein the epithelium comprises basal cell progenitors, mucus-secreting goblet cells and ciliated cells.

Embodiment 32

A method of culturing a three-dimensional pseudostratified mucociliary epithelium by (a) plating cells on a Matrigel-coated surface and (b) treating the cells with a differentiation media, wherein the epithelium comprises basal cell progenitors, mucus-secreting goblet cells and ciliated cells and wherein the mucus-secreting goblet cells and ciliated cells surround a central lumen.

Embodiment 33

A method of culturing a three-dimensional pseudostratified mucociliary epithelium by (a) plating p63$^+$NGFR$^+$ITGA6$^+$ airway basal cells on a Matrigel-coated surface and (b) treating the cells with a differentiation media, wherein the epithelium comprises basal cell progenitors, mucus-secreting goblet cells and ciliated cells.

Embodiment 34

A method of screening airway epithelium remodelling agents wherein the method comprises:
 (a) culturing a three-dimensional pseudostratified mucociliary epithelium according to any one of the embodiments 31 to 33; and
 (b) subsequently to step (a) adding to the cells a disease-mediator of goblet cell metaplasia; and
 (c) concomitantly or subsequently to adding the disease-mediator in step (b), adding to the cells an anti-remodelling agent; and wherein the anti-remodelling agent prevents goblet cell metaplasia.

Embodiment 35

A method of screening airway epithelium anti-remodelling agents according to embodiment 34 wherein the disease-mediator of goblet cell metaplasia is IL-13 and the anti-remodelling agent is an anti-Notch2 antagonist.

Embodiment 36

A method of screening airway epithelium anti-remodelling agents according to embodiment 35 wherein the anti-remodelling agent is an anti-Notch2 antibody.

Embodiment 37

A method of screening airway epithelium anti-remodelling agents according to embodiment 35 wherein the anti-remodelling agent is a fibronectin molecule against Notch2.

A fibronectin molecule, an adnectin, a DARPin, an avimer, an affibody, an anticalin, an affilin, and a protein epitope mimetic are described herein below.

The fibronectin molecule has a scaffold based preferably on fibronectin type III domain (e.g., the tenth module of the fibronectin type III (10 Fn3 domain)). In one embodiment the binding molecule is an adnectin (Adnectins®).

The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (U.S. Pat. No. 6,818,418).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

DARPins technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that bind to the target antigen using the methodology described in, for example, US20040175756; US20050053973; US20050048512; and US20060008844.

Affibody® are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate Affibody® libraries with a large number of ligand variants (See e.g., U.S. Pat. No. 5,831,012). Affibody® molecules mimic antibodies; they have a molecular weight of 6 kDa, compared to the molecular weight of antibodies, which is approximately 150 kDa. In spite of its small size, the binding site of Affibody® molecules is similar to that of an antibody.

Anticalins® are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target compounds of different shape with high affinity and specificity.

Affilin® molecules are small non-immunoglobulin proteins which are designed for specific affinities towards proteins and small molecules. New Affilin® molecules can be very quickly selected from two libraries, each of which is based on a different human derived scaffold protein. Affilin™ molecules do not show any structural homology to immunoglobulin proteins. SciI Proteins employs two Affilin™ scaffolds, one of which is gamma crystalline, a human structural eye lens protein and the other is "ubiquitin" superfamily proteins. Both human scaffolds are very small, show high temperature stability and are resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368

Protein Epitope Mimetics (PEM) are medium-sized, cyclic, peptide-like molecules (ca. 1-2 kDa) mimicking beta-hairpin secondary structures of proteins, the major secondary structure involved in protein-protein interactions.

Pharmaceutical Compositions

The invention provides for an isolated binding molecule that binds human Notch2 formulated with a pharmaceutical acceptable carrier for use in treating respiratory diseases.

In one embodiment, the isolated binding molecule for use in the invention is formulated as a composition, e.g., a pharmaceutical composition, containing one or a combination of monoclonal antibodies, formulated together with a pharmaceutically acceptable carrier. For example, a pharmaceutical composition used in the invention can comprise a combination of antibodies that bind to different epitopes of Notch2 or antibodies that have complementary activities.

Pharmaceutical compositions used in the invention also can be administered in combination therapy, i.e., combined with other agents. For example, the combination therapy can include an antibody that binds Notch2 administered concomitantly to antibiotics, steroids agents, mucolytics, bronchodilators, CFTR activity modulators, ENaC blockers; TMEM activators/potentiators; CFTR correctors; and CFTR potentiators. Suitable ENaC blockers include those disclosed in WO2009/074575 and WO2012/035158. Suitable CFTR correctors include those disclosed in WO2007/056341, WO2010/053471, WO2010/054138 and WO2012/027247. Suitable CFTR potentiators include those disclosed in WO2006/002421, WO2011/113894 and U.S. Pat. No. 8,247,436. Such combinations may be administered simultaneously or sequentially. If administered sequentially, the period between administration of each agent may be a week or less, (e.g. a day or less, 12 hours or less, 6 hours or less, 1 hour or less, 30 minutes or less). The compositions are preferably formulated at physiological pH.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). Depending on the route of administration, the isolated binding molecule, e.g., antibody, may be coated in a material to protect the binding molecule from the action of acids and other natural conditions that may inactivate the binding molecule.

Such pharmaceutical compositions may also include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals.

A "therapeutically effective dosage" of antibody that binds Notch2 according to the invention can result in a decrease in severity of disease symptoms, an increase in frequency and duration of disease symptom-free periods, or a prevention of impairment or disability due to the disease affliction.

Compositions used in the present invention can be administered by one or more routes of administration using one or more of a variety of methods known in the art. As will be appreciated by the skilled artisan, the route and/or mode of administration will vary depending upon the desired results. Routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion. Intravenous or subcutaneous administration is particularly preferred.

Alternatively, an antibody used in the invention can be administered by a non-parenteral route, such as a topical, epidermal or mucosal route of administration, for example, intranasally, orally, vaginally, rectally, sublingually or topically.

EXAMPLES

Sequences of the antibodies of the present invention exemplified herein, together with a sequence correlation table are described towards the end of this specification.

Materials and Methodology

Primary antibodies used in this study were MUC5AC (clone 45M1; Thermo Scientific), acetylated α-tubulin (clone 6-11B-1; Sigma-Aldrich), mouse anti-p63 (clone 4A4, Santa Cruz Biotechnology), rabbit anti-p63 (Abcam), ITGA6 (Go H3; Abcam), NGFR (Abcam), Ki-67 (Invitrogen). Alexa Fluor 488, 568, and 633 secondary antibodies, Alexa Fluor 647 and Rhodamine-conjugated phalloidin, and ProLong gold antifade with DAPI were obtained from Invitrogen.

For production of anti-Notch1 (α-N1), anti-Notch2 (α-N2 D3), anti-Notch2 (α-N2 59R5), and anti-Notch3 (α-N3) antibodies, DNA synthesis was carried out (Invitrogen) for light and heavy chains to correspond to published amino acid sequences ((WO2008/15025; US2010/0080808; US2008/0226621 and WO2010/05566), with the following modifications: antibody α-N1 and antibody D3 have a glutamine at the N-terminus of the heavy chain, rather than a glutamic acid as in the published sequence.

Synthetic products were subcloned into a dual CMV promoter vector (pRS5a derivative containing dihydrofolate reductase (DHFR) and neomycin resistance markers).

Stable cell lines expressing the antibodies were made by transfection of CHOK1 PD cells followed by selection for methotrexate and G418 resistance. CHO pools were maintained in selection media and expanded for protein production. The conditioned medium was clarified using a filter train of 1.2 μm filter, 0.45+0.2 μm filter, and a final 0.2 μm (Sartorius Corporation, Edgewood, N.Y.). The conditioned medium was then concentrated five- to ten-fold (Tangential Flow Filtration Device, Tangenx Corporation, Shrewsbury, Mass.) and applied to MabSelect SuRe (GE Healthcare, USA) equilibrated in phosphate buffered saline (PBS).

The IgG1 antibody molecules were eluted using 50 mM citrate pH 3.0, fractions were immediately neutralized by dialysis into 1xdPBS (Slide-A-Lyzer Dialysis Cassette, Pierce Corporation) into PBS.

Protein aggregation was measured by HPLC (Shimadzu) on an analytical sizing column (Tosoh 3000SWXL) and further polished on a Superdex 200 column (GE Healthcare, USA) if necessary.

Antibodies were concentrated using centrifugation spin columns (Vivaspin, GE Healthcare, USA) and tested for endotoxin values using an Endosafe PTS reader (Charlesriver, USA) prior to use.

Human Tissue Culture

Human bronchial epithelial (HBE) cells and culture media were obtained from Lonza. Air-liquid interface cultures using passage 2 (P2) cells were performed as previously described (Danahay, H. et al., American journal of physiology. Lung cellular and molecular physiology 282, L226-236 (2002)). For three-dimensional culturing of HBE cells, P1 cells were trypsinized and resuspended (30,000 cells/ml) in HBE differentiation media containing 5% growth factor-reduced Matrigel (BD Biosciences). 20 μl of suspension was plated in each well of a 384-well plate (Greiner) pre-coated with 10 μl of a 25% solution of Matrigel (BD Biosciences) in HBE differentiation media. Wells were fed or treated at day 2 and day 8 of culture by adding 30 μl of differentiation media containing the appropriate treatment. Three-dimensional cultures were analyzed at the time points indicated.

Microscopy

Immunofluorescence of HBEC bronchospheres was performed as described previously for MCF10A cysts (Debnath, J. et al., Methods 30, 256-268 (2003) with the following modifications. After incubation with fluorescence-conjugated secondary antibodies, DNA was stained with a 1:1 mix of PBS and ProLong gold antifade containing DAPI. Confocal microscopy was performed at room temperature on a microscope (Zeiss LSM510 Meta) using an EC Plan-Neofluar 10×/0.30 dry objective (Zeiss), an EC Plan-Neofluor 20×/0.5 dry objective (Zeiss), a C-Apochromat 40×/1.2 W corr (Zeiss), or a C-Apochromat 63×/1.2 W Corr objective (Zeiss). Images were collected with Zen confocal software (Zeiss). Scale bars were added, and images were processed using Zen (Zeiss) and Photoshop (Adobe). Air-liquid interface (ALI) cultures were processed for immunofluorescence analysis after 14 days of culture at ALI by rinsing the apical surface of each filter with PBS, and then fixing in 4% paraformaldehyde for 4 hours. Filters were washed with IF buffer (130 mM NaCl, 7 mM $Na_2HPO_4$, 3.5 mM $NaH_2PO_4$, 7.7 mM $NaN_3$, 0.1% bovine serum albumin, 0.2% Triton X-100, 0.05% Tween-20), blocked with IF wash containing 10% goat serum, and stained with primary antibody in IF wash containing 10% goat serum overnight at 4° C. Secondary antibodies were used at a 1:200 dilution in IF buffer containing 10% goat serum. To quantify the total staining area of ALI cultures, 10×13 images were collected with a plan Neofluar 10×0.3 NA Ph1 objective (EC; Carl Zeiss, Inc.) on a microscope (Axiovert 200; Carl Zeiss, Inc.) equipped with a motorized stage and a camera (Orca-ER-1394; Hamamatsu Photonics) controlled by Axiovision software (Carl Zeiss, Inc.) and used to generate a single composite image using the MOSAIX function in Zeiss Axiovision. Quantification of the total staining area was performed with ImageJ. Two to three regions of each ALI culture were punched out with a 4 mm biopsy punch (Miltex, Inc.) and mounted in ProLong gold antifade containing DAPI for imaging by confocal microscopy on a microscope (Axiovert 200; Carl Zeiss, Inc.) equipped with a motorized stage, a Yokogawa CSU-X1 spinning disc head, and an EMCCD camera (Evolve 512, Photometrics), with a Plan-Apochromat 100×/1.4 Oil DIC objective (Zeiss). Cells positive for MUC5AC, MUC5B, or cilia (acetylated α-Tubulin) staining were counted manually. For time-lapse video microscopy, HBECs were imaged at the indicated times during bronchosphere development at 37° C. with a plan Neofluar 10×0.3 NA Ph1 objective (EC; Carl Zeiss, Inc.). Images were taken every 5 min for the indicated time period. Annotations (time stamp and scale bar) were added and videos were assembled using Axiovision software.

RNA Isolation and Quantitative PCR

RNA was isolated from 3D bronchosphere cultures with Trizol (Invitrogen), using manufacturer's specifications. To isolate RNA from mouse tissue, approximately 20 mg of tissue was placed in a 1.5 ml eppendorf tube with 1 ml of Buffer RLT Plus (Qiagen). A 5 mm stainless steel bead (Qiagen) was added to the tube, and the tissue was sheared using a Tissue Lyser II (Qiagen). RNA from the sheared tissue was purified using the RNeasy Plus Mini Kit (Qiagen), using manufacturer's specifications. TaqMan Reverse Trascription Reagents (Invitrogen) were used to generate cDNA from 1 μg of total RNA. Quantitative PCR was performed on a ViiA7 Real-Time PCR System (Applied Biosystems), using 40 ng of cDNA per reaction with the following Taqman probes (Applied Biosystems): MUC5AC, Hs01365601_m1; MUC5B, Hs00861588_m1; FOXA3, Hs00270130_m1; FOXJ1, Hs00230964_m1; DNAI2, Hs01001544_m1; TP63, Hs00978340_m1; ITGA6, Hs01041011_m1; GAPDH, Hs99999905_m1; Muc5ac, Mm012718_m1; Foxj1, Mm012367279_m1; Trp63, Mm00495788_m1; Gapdh, Mm99999915_g1.

Results

Human Bronchial Epithelial Cells Form 'Bronchospheres' in 3D Culture

Human bronchial epithelial (HBE) cells have been used extensively as polarized monolayers grown at air-liquid interface (ALI), although at least one study has been performed in three dimensions. Human bronchial epithelial cells (HBECs) were grown in chambered slides and stained for integrin α6 (ITGA6, green), p63 (orange), nerve growth factor receptor (NGFR, red), and DNA (blue). HBE were found to express the basal cell markers p63, NGFR, and ITGA6 (FIG. 1a). Within 14 days of seeding p63$^+$NGFR$^+$ITGA6$^+$ HBE cells in Matrigel, the cells formed cyst-like structures with a central lumen (FIG. 1b). A comparison of the expression of cell type-specific markers by qPCR highlighted the differentiation of the basal cells into a mucociliary epithelium, with the appearance of markers of ciliated (FOXJ1, DNAI2) and goblet cells (MUC5AC, MUC5B, FOXA3) (FIG. 1c). Immunostaining further revealed p63$^+$ cells basal to the cells lining the interior of the cyst that would be consistent with a pseudostratified structure (FIG. 1d). These p63$^+$ cells were often Ki67$^+$ (a marker of proliferation) consistent with basal cell proliferation in the mature bronchosphere structure (data not shown). In contrast, cells lining the central lumen were invariably negative for Ki67 staining. Ciliated cells, detected by acetylated α-tubulin staining, were identified lining the central lumen. Furthermore, prior to fixation, the rapid beating of these cilia could be observed under bright field conditions. In addition to ciliated cells, MUC5AC$^+$ and MUC5B$^+$ goblet cells were also identified lining the central lumen (FIG. 1d). MUC5AC$^+$ and MUC5B$^+$ material was also seen inside of the central lumen consistent with secretion of mucins by the epithelium in addition to their storage (FIG. 1d and data not shown). With the knowledge that bronchospheres were composed of at least three cell types: basal, ciliated and goblet, we asked whether this heterogeneity was a consequence of mixed populations of pre-committed basal cells forming a bronchosphere or whether the basal cells were indeed pluripotent, as has been described in the murine trachea (Rock, J. R. et al., Proceedings of the National Academy of Sciences of the United States of America 106, 12771-12775 (2009)). Human airway basal cells labeled with Oregon Green 488 Carboxylic Acid Diacetate (carboxy-DFFDA; Invitrogen®) were mixed with an equal amount of unlabeled cells, plated in 3D at different seeding densities and imaged after 3 days in culture. A clonal seeding threshold was established to be 75 cells/well of a 384 well plate using a mixture of labeled and unlabeled cells (FIG. 1e). At seeding densities of 75 cells per well and lower, structures are clonal, exclusively containing either labeled or unlabelled cells, with bronchospheres forming with an approximate 40% clonal efficiency. Bronchospheres were observed to be composed of basal, goblet, and ciliated cells, confirming the pluripotent nature of p63$^+$NGFR$^+$ITGA6$^+$ HBE cells (FIG. 1f).

IL-13 Induces a Mucus Hypersecretory Phenotype in Bronchospheres

Figure 2:
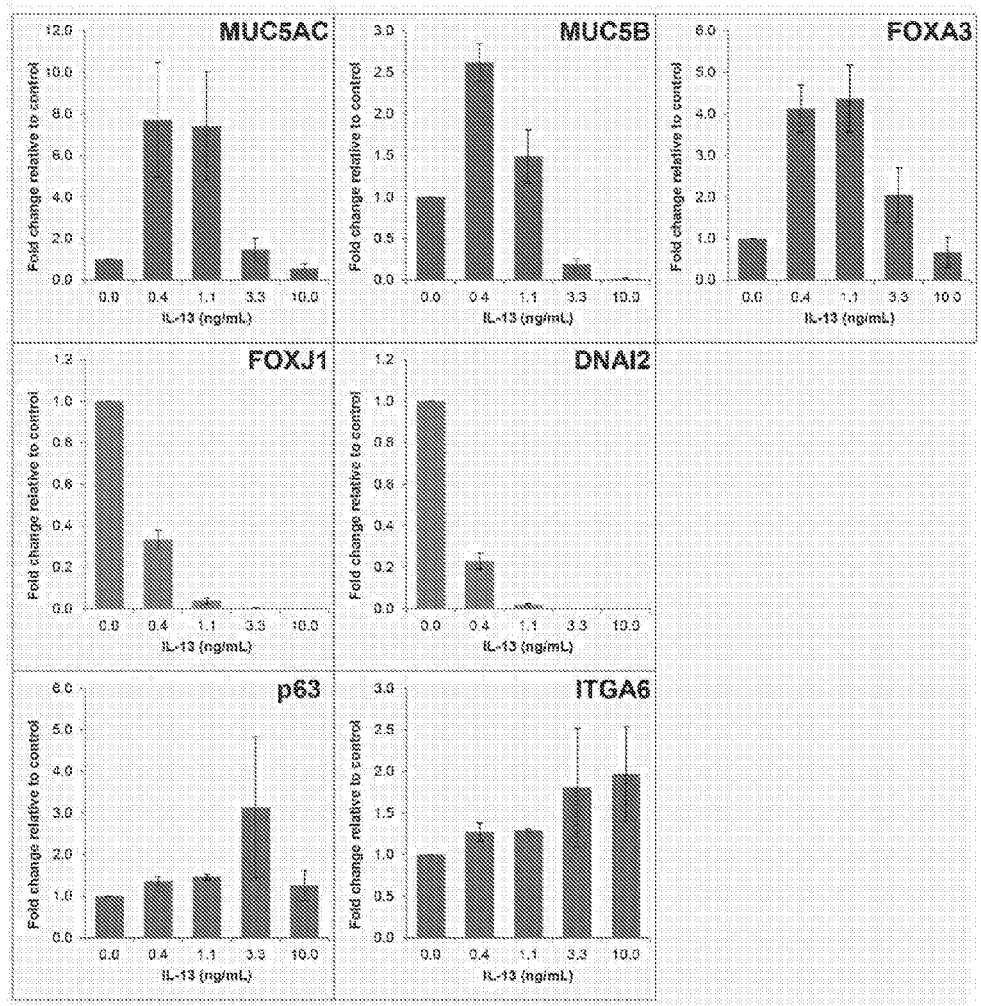
FIG. 2: IL-13 treatment promotes goblet cell formation at the expense of ciliated cells. (a) Quantitative PCR analysis of expression levels of cell type-specific markers of goblet (MUC5AC, MUC5B, FOXA3), ciliated (FOXJ1, DNAI2) and basal cells (p63, ITGA6) in 3D bronchospheres grown in the presence of increasing concentrations of IL-13. Shown is the average fold change+/−SEM relative to control from five independent experiments. (b) Bronchospheres grown in the presence of vehicle control or (c) 1 ng/ml of IL-13 at day 14 and stained for DNA (blue), acetylated α-Tubulin (orange), MUC5AC (green), and actin (red). Scalebar=25 µm.
Figure 2:
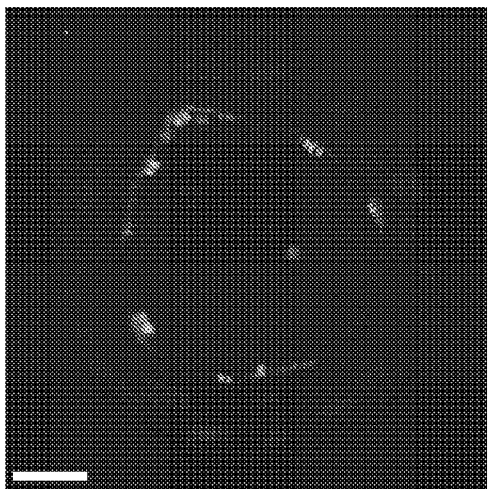
Figure 2:
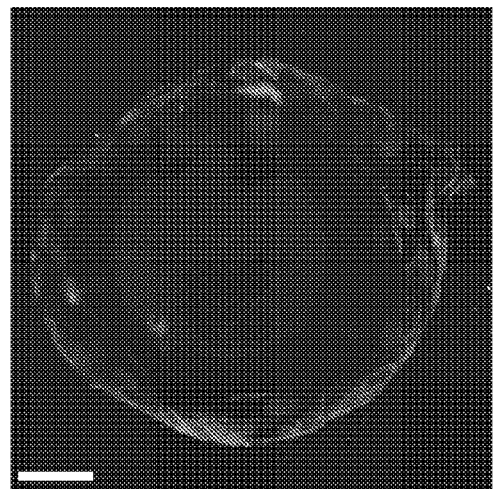

IL-13 has been shown to be a key mediator of asthmatic phenotypes with several groups demonstrating that IL-13 acts directly on the epithelium to drive a goblet cell metaplasia phenotype. Following treatment of bronchospheres with IL-13 between days 2 and 14 after seeding there was a clear enhancement in the expression of markers of goblet cells, while ciliated cell marker expression declined, as measured by qPCR (FIG. 2a). The remodelled phenotype was concentration dependent, and bell-shaped, consistent with previous observations using ALI HBE cultures (Atherton, H. C. et al.; American journal of physiology. Lung cellular and molecular physiology 285, L730-739 (2003)). Concentrations of IL-13>3 ng/mL were toxic and disrupted bronchosphere formation (data not shown). HBE cultures treated with vehicle control contained many ciliated cells, as revealed by immunostaining for acetylated α-tubulin which labels the cilia (FIG. 2b). In IL-13 treated bronchospheres the enhanced expression of goblet cell markers was accompanied by the accumulation of secreted mucins in the central lumen during culture (FIG. 2c). The loss of ciliated cell marker expression was confirmed by a lack of acetylated α-tubulin positive structures in the IL-13 treated bronchospheres (FIG. 2c). These data show that the bronchospheres were able to respond to established inducers of airway epithelial remodeling.

Inflammatory Cytokines Alter Basal Cell Fates

A number of inflammatory cytokines and growth factors have been reported to increase the expression of MUC5AC in airway epithelial cells, a mucin that is up-regulated in a number of airway diseases, including asthma and COPD. However, the mechanism by which soluble factors lead to increased MUC5AC levels is poorly understood. A small collection of 55 secreted, recombinant human proteins (Table 1) was profiled in the bronchosphere assay using markers of goblet cells (MUC5AC, MUC5B, FOXA3), ciliated cells (FOXJ1, DNAI2) and basal cells (p63, ITGA6) to monitor the changes in the abundance of each cell type. Proteins were initially tested at 3 concentrations (3.3, 10 and 30 ng/mL) and those displaying evidence of activity against any of the expression markers were repeated with an expansion of the concentration range if deemed necessary. Of the 55 proteins, IL-13, IL-17A, IL-1a, IL1-β, IL-28A, IL-28B, IL-29, IFN-α-2, IFN-γ and FGF-7 showed a concentration-dependent change in expression of at least one cell-type marker. On validation, IL-13, IL-17A, IL1-α, IL1-β, IL-28A, IL-28B, IL-29, IFN-α-2 and IFN-γ induced a robust change in expression of at least one of the cell-type markers. FGF7 enhanced the expression of MUC5B without affecting any of the other markers. Each of the other protein effectors (IL-13, IL-17A, IL-1a, IL-1β, IL-28A, IL-28B, IL-29, IFN-α-2, and IFN-γ) enhanced the expression of at least two of the goblet cell markers and attenuated expression of both of the ciliated cell markers. These results suggest that similar to IL-13, several other inflammatory cytokines can bias the differentiation of basal cells away from a ciliated cell fate and towards a goblet cell.

TABLE 1

| | |
|---|---|
| BMP2 | IL-10 |
| BMP4 | IL-12 |
| BMP7 | IL-13 |
| CCL5 | IL-15 |
| CHI3L1 | IL-16 |
| FGF-10 | IL-17A |
| FGF-16 | IL-18 |
| FGF-19 | IL-19 |
| FGF-6 | IL-1α |
| FGF-7 | IL-1β |
| FGF-8 | IL-2 |
| FGF-9 | IL-20 |
| HBEGF | IL-21 |
| HGF | IL-22 |
| IFN-α-2 | IL-23 |

TABLE 1-continued

| | |
|---|---|
| IFN-γ | IL-24 |
| IGF2 | IL-26 (di) |
| IL-26 (mono) | NRG2 |
| IL-27 | PBS |
| IL-28A | TGFβ1 |
| IL-28B | TNF-α |
| IL-29 | IL-35 |
| IL-3 | IL-4 |
| IL-31 | IL-5 |
| IL-32α | IL-6 |
| IL-32γ | IL-8 |
| IL-33 | LT-α |
| IL-34 | NRG1 |

IL-17a Treatment Biases Basal Cell Differentiation Towards a Goblet Cell

Figure 3:
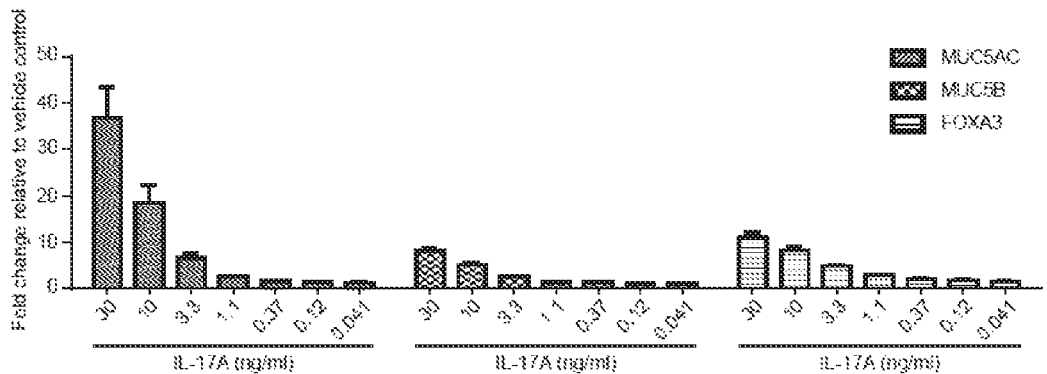
FIG. 3: Multiple inflammatory cytokines bias basal cell fate towards a goblet cell and away from a ciliated cell. Quantitative PCR analysis of expression levels of cell type-specific markers of (a) goblet cells (MUC5AC, MUC5B, FOXA3), (b) ciliated cells (FOXJ1, DNAI2) and (c) basal cells (p63, ITGA6) in 3D bronchospheres grown in the presence of increasing concentrations of IL-17A. Shown is the mean fold change+/−SEM relative to control from three independent experiments. (d) Quantification of the total staining area for MUC5AC, MUC5B, and acetylated α-Tubulin of human airway basal cells grown on filters at air-liquid interface, with or without IL-17A (10 ng/ml). Shown is the average fold change+/−SEM relative to control from three independent experiments, each performed in duplicate. (e) Quantification of the number of cells staining positive for markers of goblet cells (MUC5AC, MUC5B) or ciliated cells (acetylated α-Tubulin) from four independent regions of each filter from the experiments shown in (d). A total of more than 700 cells were counted from control and IL-17A-treated filters, respectively. Shown is the percentage of cells stained for each marker.
Figure 3:
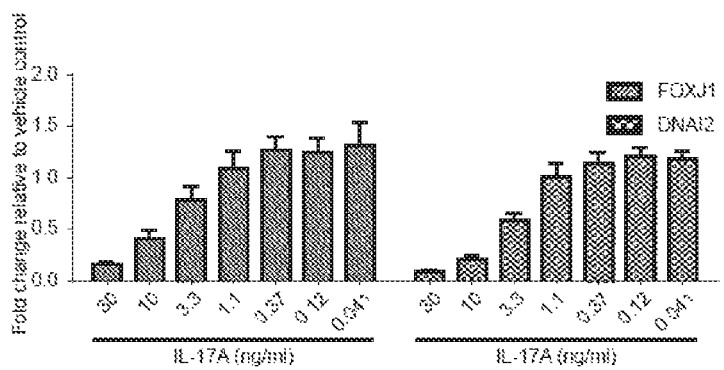
Figure 3:
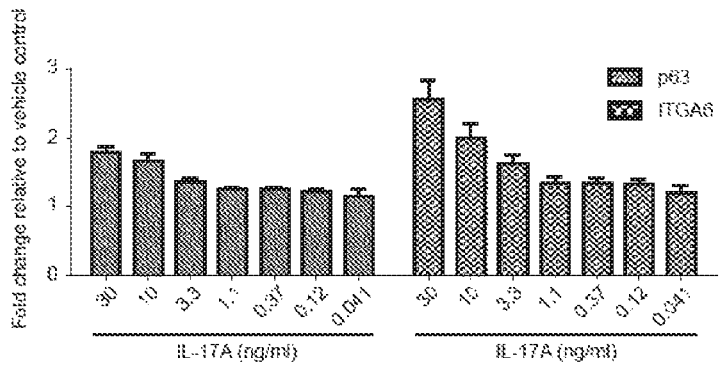
Figure 3:
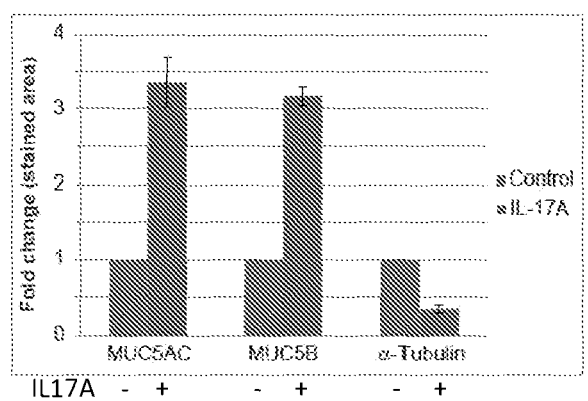
Figure 3:
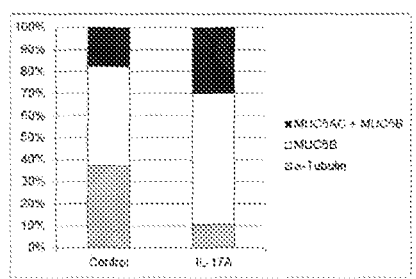

Of the mediators demonstrated to influence the differentiation of the bronchospheres, IL-17A has been reported to play a critical role in allergic asthma (Souwer, Y. et al. Current opinion in immunology 22, 821-826 (2010)). IL-17A is a cytokine that is secreted by Th17 cells, and has been shown to stimulate mucin gene expression in cultured airway epithelial cells (Chen, Y., et al. The Journal of biological chemistry 278, 17036-17043 (2003)) and enhance airway smooth muscle contraction in vivo (Kudo, M., et al. Nature medicine 18, 547-554 (2012)). The results from our screen and subsequent validation using a broader range of IL-17A concentrations indicated that in addition to increasing MUC5AC levels, IL-17A treatment resulted in increased levels of multiple markers of goblet cells (MUC5B and FOXA3) (FIG. 3a), while inhibiting the expression of markers of ciliated cells (FOXJ1 and DNAI2) (FIG. 3b), as measured by qPCR. No significant changes were observed for basal cell markers (FIG. 3c). These results suggest that IL-17A treatment can bias the differentiation of the airway basal cell towards a goblet cell at the expense of a ciliated cell, a phenotype similar to the goblet cell metaplasia seen in many airway diseases. These data were further confirmed with air-liquid interface (ALI) cultures, seeding airway basal cells onto trans-well filters, and treating the cultures from day 7 (day 0 at ALI), prior to the initiation of differentiation, with IL-17A and analyzing the resulting phenotype at day 21 (day 14 at ALI). While cultures grown under control conditions contained a mixture of goblet and ciliated cells at day 21, IL-17A-treated cultures had a profound expansion of the goblet cell population as indicated by the increased expression of the MUC5AC and MUC5B markers, together with a dramatic reduction in the number of ciliated cells indicated by the decreased expression of the α-tubulin marker (FIGS. 3d and 3e).

Figure 4:
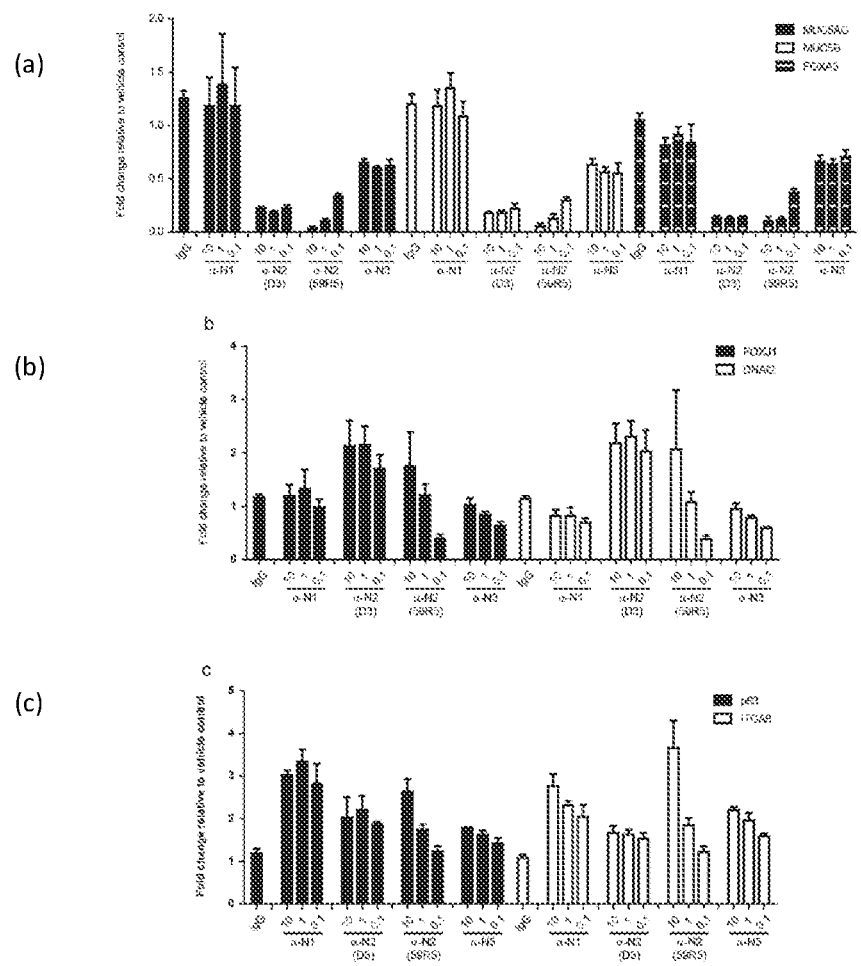
FIG. 4: Effect of selective antibody blocking of individual Notch receptors on airway basal cell fate decisions in vitro. Human airway basal cells grown in 3D in the presence of vehicle control, IgG, or increasing concentrations of antagonist antibodies specific for Notch1 (α-N1), Notch2 (α-N2), or Notch3 (α-N3), and analyzed for the expression levels of the indicated goblet cell markers (a), ciliated cell markers (b), and basal cell markers (c) by quantitative PCR. Shown is the mean fold change+/−SEM relative to control from at least three independent experiments.

Notch2 is Required for Cytokine-Driven Effects on Basal Cell Fate Specification In Vitro The Notch signaling pathway plays a key role in the determination of cell fate in multiple tissues throughout development and several studies have found a role for Notch signaling in regulating the choice between secretory and ciliated cells during development and repair. We treated developing 3D bronchosphere cultures with Notch receptor-specific blocking antibodies (Wu, Y., et al. Nature 464, 1052-1057 (2010)). While anti-Notch1 and anti-Notch3 antibodies had little effect on the differentiation of goblet or ciliated cells in 3D bronchosphere cultures, antibodies against Notch2 inhibited goblet cell formation while potentiating ciliated cell formation. As shown in FIGS. 4a and 4b, specific anti-Notch2 Ab D3 and 59R5 decreased the expression of goblet cell markers MUC5AC, MUC5B and FOXA3 whilst increasing the expression of ciliated cells markers FOXJ1 and DNAI2 when compared with IgG control, or with anti-Notch1 or anti-Notch3 antibodies, as measured by qPCR. Neither antibody showed any significant effect on basal cell markers p63 and ITGA6 (FIG. 4c).

Figure 5:
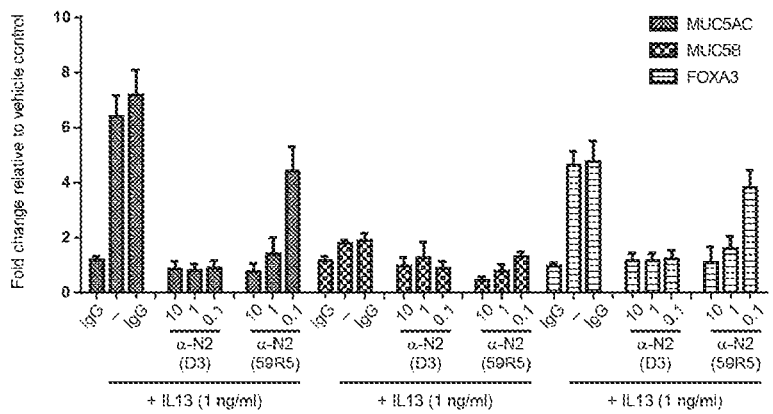
FIG. 5: Notch2 inhibition alters cell fate away from a goblet cell and towards a ciliated cell. Quantitative PCR analysis of the expression levels of goblet cell markers (a), ciliated cell markers (b), and basal cell markers (c) in 3D bronchospheres grown in the presence of vehicle control or 10 µg/ml IgG, with or without 1 ng/ml IL-13, or increasing concentrations (in µg/ml) of Notch2 antagonist antibodies (α-N2 D3 and 59R5) together with 1 ng/ml of IL-13. Shown is the mean fold change+/−SEM relative to control from at least four independent experiments.
Figure 5:
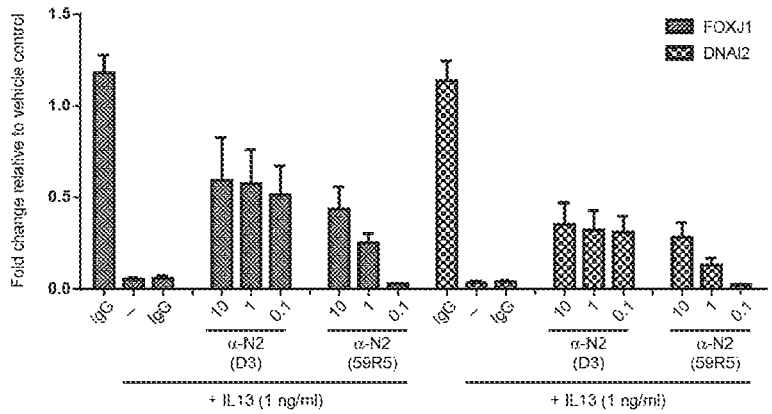
Figure 5:
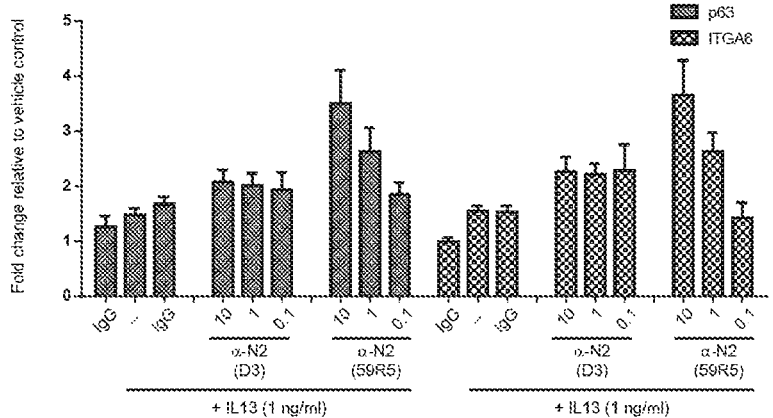

In order to understand if neutralizing Notch2 could prevent goblet cell metaplasia, a hallmark of several airway diseases including asthma, cystic fibrosis, and COPD, anti-Notch2 antibodies were tested for their effect on IL-13-driven goblet cell metaplasia in 3D bronchospheres. Human airway basal cells were grown in 3D in the presence of vehicle control or IgG, with or without 1 ng/ml IL-13, or increasing concentrations of α-N2 D3 or 59R5 antibodies together with 1 ng/ml of IL-13, and analyzed by qPCR for the expression levels of the indicated goblet cell markers (FIG. 5a), ciliated cell markers (FIG. 5b), and basal cell markers (FIG. 5c). Anti-Notch2 specific antibodies completely inhibited IL-13-driven goblet cell metaplasia in 3D bronchospheres (FIG. 5a) and ALI cultures (results not shown) as revealed by the decreased expression of goblet cell markers MUC5AC, MUC5B and FOX3A. Moreover, anti-Notch2 D3 and 59R5 antibodies partially restored ciliated cells function as shown by the increased expression of ciliated cell markers FOXJ1 and DNAI2 (FIG. 5b). No effect was observed on basal cells markers p63 and ITGA6 (FIG. 5c), indicating that the effect of IL-13 on basal cell fate requires Notch2 activation.

Notch2 is Required for Cytokine-Driven Effects on Basal Cell Fate Specification In Vivo Female Balb/c mice (20-25 g) were obtained from Charles River (Morgate, UK). Mice were housed under specific pathogen free conditions and were provided with food and water ad libitum. Experiments were performed in accordance with the UK Animals Scientific Procedures Act 1986.

Mice received 0.5 μg of recombinant mouse IL-13 (Ebiosciences, UK) or phosphate-buffered saline (PBS) intranasally on 3 consecutive (days 1, 2, 3). Mice received either 20 mg/kg neutralizing antibody against Notch2 (α-N2 D3 or α-N2 59R5) or control IgG, or PBS intraperitoneally 2 hours before intranasal challenge with either IL-13 or PBS, on days 1 and 3 only. Mice were euthanized 24 hours after the final IL-13 administration. The left lungs were excised, inflated with 10% neutral buffered formalin (NBF) and preserved in NBF. Lungs were embedded in paraffin wax and lung sections were obtained for each animal. Sections were stained with Periodic Acid-Schiff (PAS) stain for mucus.

PAS positive staining was quantified in lung sections using Definiens Image Analysis software. Two distinct lung sections were analyzed per mouse and the total area of PAS positive staining within the sections was determined. The PAS positive staining was normalized to the area of tissue analyzed and represented as 'Relative Area PAS Positive Mucus (%)'.

Data are expressed as mean±SEM. Statistical significance was determined using a parametric one way ANOVA and Dunnetts post-test. GraphPad Prism (version 5.04) was used to generate graphs and perform statistical analysis. ***$p<0.001$ denotes statistically significant difference from relevant isotype control group.

Figure 6:
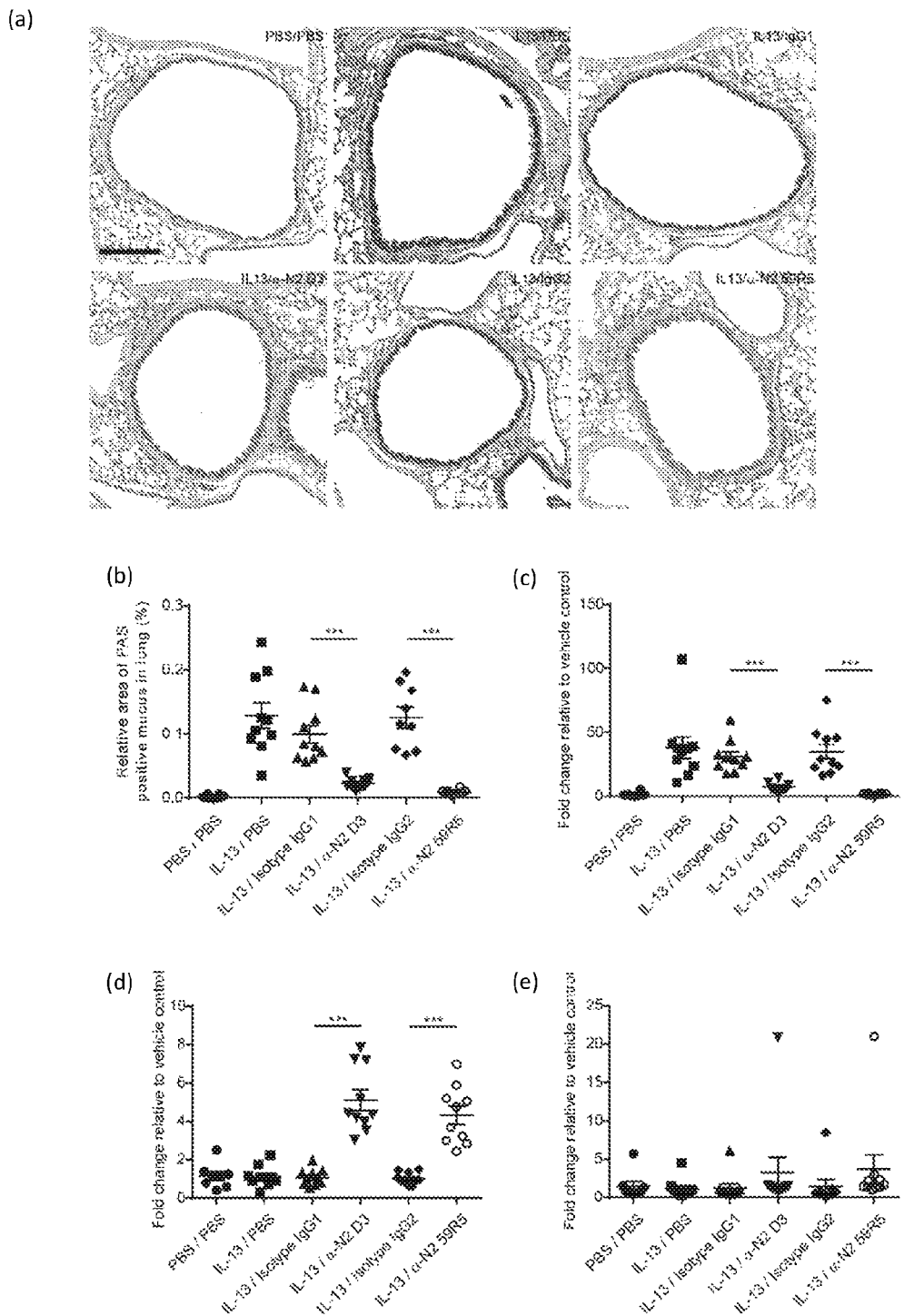
FIG. 6: Neutralization of Notch2 inhibits IL-13-driven goblet cell metaplasia in vivo. (a) Representative images of PAS-stained lung sections from the indicated treatment groups. Scalebar=200 µm. (b) Quantification of the relative area of PAS staining in the lung. (c-e) Quantitative PCR analysis of goblet (Muc5ac, c), ciliated (Foxj1, d), and basal cell (Trp63, e) marker expression in lungs from the indicated treatment groups. ***$p<0.001$ denotes statistically significant difference from relevant isotype control group by One-way ANOVA and Dunnett's Multiple Comparison Test.

PAS staining of lung sections revealed that IL-13 treatment drove a goblet cell metaplasia phenotype in vivo, as previously reported (Kuperman, D. A. et al., Nature medicine 8, 885-889 (2002), while vehicle control had no effect (FIGS. 6a and b). Co-administration of anti-Notch2 antibodies (D3 or 59R5) completely blocked IL-13 driven goblet cell metaplasia, as evidenced by reduced PAS staining of lung sections (FIGS. 6a and 6b). We verified this observation using qPCR analysis of Muc5ac expression levels from RNA isolated from whole lung tissue (FIG. 6c), and also found that inhibition of Notch2 resulted in a concomitant increase in the ciliated cell marker Foxj1 (FIG. 6d), while having no effect on the basal cell marker Trp63 (FIG. 6e). Together, these data indicate that Notch2 is required for IL-13 driven goblet cell metaplasia in vitro and in vivo and that neutralization of Notch2 function prevents cytokine driven goblet cell metaplasia.

Therapeutic Treatment with Anti-Notch2 Antibody In Vivo (IL-13 Mouse Model)

Female Balb/c mice (20-25 g) were obtained from Charles River (Morgate, UK). Mice were housed under specific pathogen free conditions and were provided with food and water ad libitum. Experiments were performed in accordance with the UK Animals Scientific Procedures Act 1986.

Mice received 0.5 µg of recombinant mouse IL-13 (Ebiosciences, UK) or phosphate-buffered saline (PBS) intranasally on 10 consecutive (days 1-10). Mice received either 20 mg/kg neutralizing anti-Notch2 antibody α-N2 (antibody D3 above) or isotype control IgG, intraperitoneally 2 hours before intranasal challenge with either IL-13 or PBS, on days 4, 6, 8 & 10 only. An additional group of mice received 0.5 µg of recombinant mouse IL-13 (Ebiosciences, UK) or phosphate-buffered saline (PBS) intranasally on 3 consecutive (days 1-3) only.

Mice were euthanized 24 hours after their final PBS or IL-13 administration. The left lungs were excised, inflated with 10% neutral buffered formalin (NBF) and preserved in NBF. Lungs were embedded in paraffin wax and lung sections obtained for each animal. Sections were stained with PAS stain for mucus.

PAS-positive staining was quantified in lung sections using Definiens Image Analysis software. Two distinct lung sections were analyzed per mouse and the total area of PAS positive staining within the sections was determined. The PAS positive staining was normalized to the area of tissue analyzed and represented as 'Relative Area PAS Positive Mucus (%)'.

Data are expressed as mean±SEM. Statistical significance was determined using a parametric one way ANOVA and Dunnetts post-test. GraphPad Prism (version 5.04) was used to generate graphs and perform statistical analysis. ***$p<0.001$ denotes statistically significant difference from the isotype control group.

Figure 7:
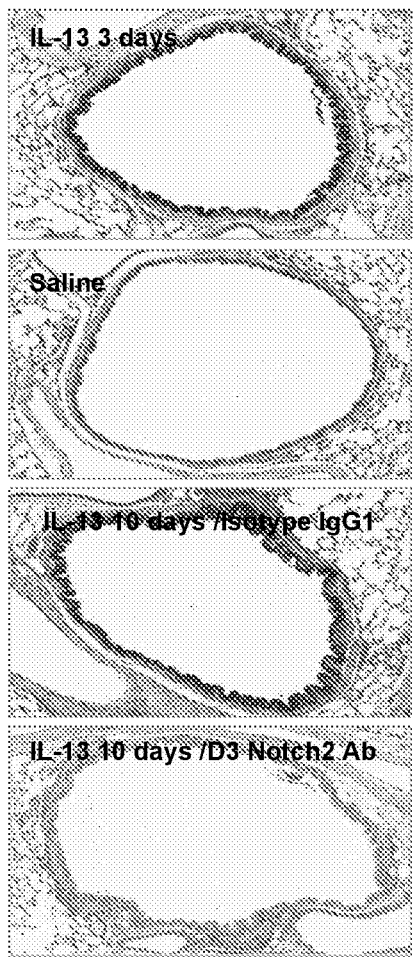
FIG. 7: Neutralization of Notch2 reverses an established IL-13-driven goblet cell metaplasia in vivo. (a) Representative images of PAS-stained lung sections from the IL-13 mouse model. (b) Quantification of the relative area of PAS staining in the lung. (c) Quantitative PCR analysis of goblet (Muc5ac, top), ciliated (Foxj1, middle), and basal cell (Trp63, bottom) marker expression in lungs from the IL-13 animal model. *$p<0.05$, ***$p<0.001$ denotes statistically significant difference from relevant isotype control group by One-way ANOVA and Dunnett's Multiple Comparison Test.
Figure 7:
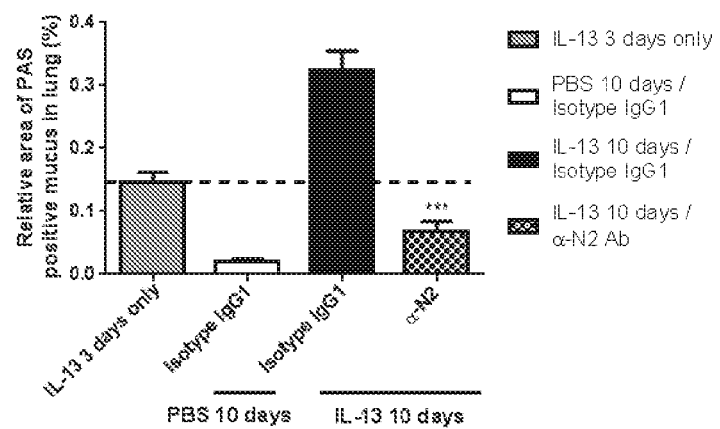
Figure 7:
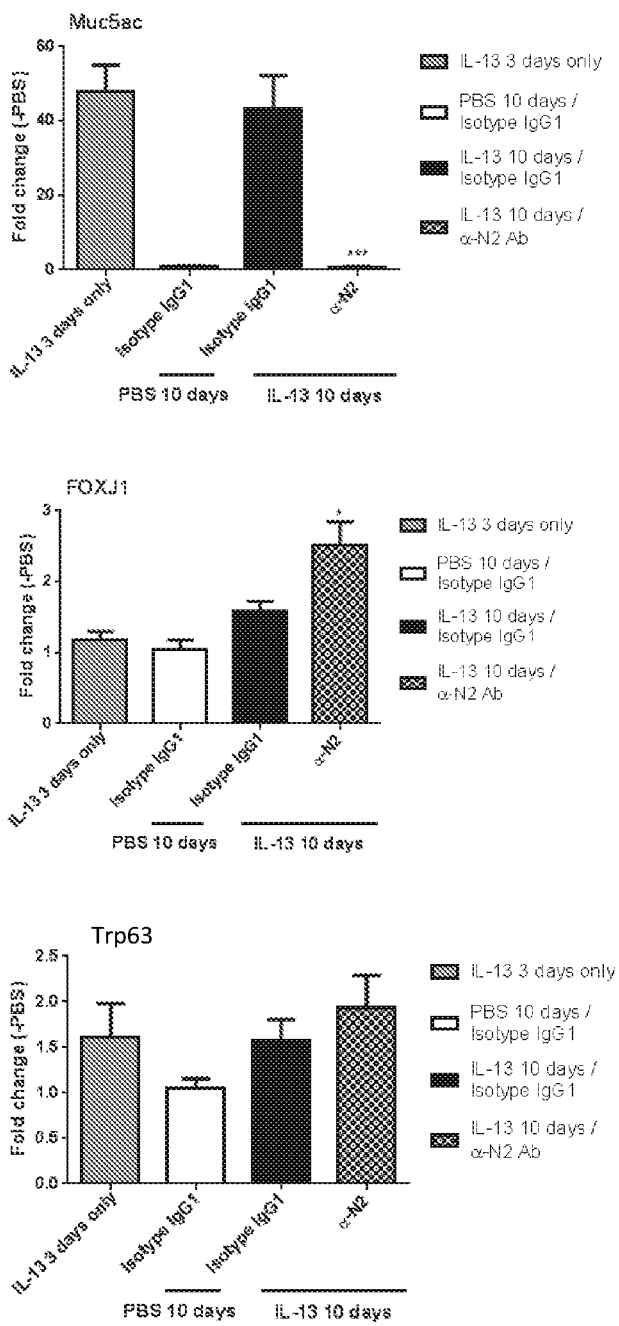

PAS staining of lung sections revealed that IL-13 treatment for 3 days only drove a goblet cell metaplasia phenotype in vivo (FIG. 7a, first panel from the top and FIG. 7b). PAS staining of lung sections revealed that IL-13 treatment for 10 days resulted in an increased level of goblet cell metaplasia (FIG. 7a, third panel from the top and FIG. 7b), compared to the group that had received only 3 days of IL-13 treatment.

Therapeutic administration of anti-Notch2 antibody was initiated after the onset of goblet cell formation (from day 4 onwards), in order to determine whether treatment would impact on an established goblet cell formation. Treatment with the anti-Notch2 antibody using a therapeutic dosing regimen reversed an established goblet cell formation, as evidenced by a profoundly reduced PAS staining of lung sections (FIG. 7a, bottom panel and FIG. 7b).

We verified this observation using qPCR analysis of Muc5ac expression levels from RNA isolated from whole lung tissue and also found that inhibition of Notch2 resulted in a concomitant increase in the ciliated cell marker Foxj1 (FIG. 7c top and middle graphs), while having no effect on the basal cell marker Trp63 (FIG. 7c bottom graph). Together, these data indicate that Notch2 is required for IL-13 driven goblet cell metaplasia in vivo and that treatment with an anti-Notch2 antibody in a therapeutic setting (after the onset of goblet cell metaplasia) can reverse an established goblet cell metaplasia in vivo. Hence, anti-Notch2 antibodies can be used to treat respiratory diseases characterized by goblet cell metaplasia and enhanced mucus hyper-secretion, such as asthma and COPD.

Therapeutic Treatment in a Chronic House Dust Mite Model

Female Balb/c mice (20-25 g) were obtained from Charles River (Morgate, UK). Mice were housed under specific pathogen free conditions and were provided with food and water ad libitum. Experiments were performed in accordance with the UK Animals Scientific Procedures Act 1986.

Mice received 25 µg of house dust mite (HDM; *D.pteronyssinus*, Greer laboratories, US) or saline intranasally on 5 days a week for 5 weeks (days 1-5, 8-12, 15-19, 22-26, 29-31). Mice received either 20 mg/kg neutralizing anti-Notch2 antibody α-N2 (antibody D3 above) or isotype control IgG, intraperitoneally 2 hours before intranasal challenge with HDM on days 22, 24, 26, 28 and 30 only.

Mice were euthanized 24 hours after their final saline or HDM administration (day 32). The left lungs were excised, inflated with 10% neutral buffered formalin (NBF) and preserved in NBF. Lungs were embedded in paraffin wax and lung sections obtained for each animal. Mucins were detected within the airways of the sections by a two-stage immunoperoxidase method using *Ulex Europaeus* agglutinin-1 (UEA-1) (Sigma, UK).

UEA-1 levels were assessed in the lung sections using Imaging Associates KS400 version 3.0 image analyser. Ten airways were analyzed per mouse and the area of UEA-1 positive staining within the airways was determined. The UEA-1 positive staining was normalized to the area of airway analyzed and represented as 'UEA-1 stained area per micron of epithelia'.

Data are expressed as mean±SEM. Statistical significance was determined using a parametric one way ANOVA and Dunnetts post-test. GraphPad Prism (version 5.04) was used to generate graphs and perform statistical analysis. ***$p<0.001$ denotes statistically significant difference from the isotype control group.

Figure 8:
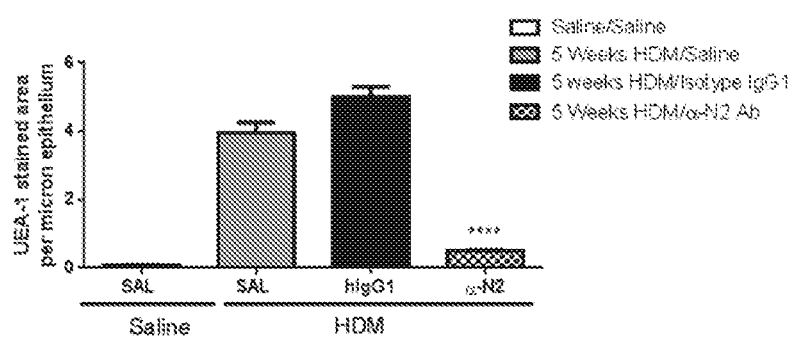
FIG. 8: Neutralization of Notch2 reverses house dust mite-induced goblet cell formation in vivo. Shown is the quantification of the relative area of UEA-1 staining in the lung. ****$p<0.0001$ denotes statistically significant difference from relevant isotype control group by One-way ANOVA and Dunnett's Multiple Comparison Test.

*Ulex Europaeus* Agglutinin-1 (UEA-1) staining of lung sections revealed that 5 weeks treatment with house dust mite drove a goblet cell metaplasia phenotype in vivo (FIG. 8). Therapeutic administration of anti-Notch2 antibody was initiated after 3 weeks of HDM challenge, in order to determine whether treatment would impact on HDM induced goblet cell formation. Treatment with the anti-Notch2 antibody using a therapeutic dosing regimen reversed goblet cell formation, as evidenced by a profoundly reduced UEA-1 staining of lung sections (FIG. 8). These data demonstrate that the anti-Notch2 antibody reduces goblet cell metaplasia driven by house dust mite.

The invention claimed is:

1. A method of treating a patient having a respiratory disease characterized by excessive goblet cell formation and mucus hyper-secretion comprising administering to the patient a therapeutically effective amount of an antibody, or antigen-binding fragment thereof, that binds to and inhibits human Notch-2.

2. The method according to claim 1, wherein the antibody binds human Notch2 extracellular domain or a soluble human Notch2 fragment.

3. The method according to claim 1, wherein the antibody does not cross-react with Notch1, Notch3 or Notch4.

4. The method according to claim 1, wherein the antibody is formulated with a pharmaceutically acceptable carrier.

5. The method according to claim 1, wherein the antibody is selected from antibody D3, antibody 59R5, or a functional fragment thereof.

6. The method of claim 1, wherein the respiratory disease is selected from cystic fibrosis (CF), primary ciliary dyskinesia, chronic bronchitis, chronic obstructive pulmonary disease (COPD), asthma or respiratory tract infections.

7. A method of treating a patient having a respiratory disease selected from cystic fibrosis (CF), primary ciliary dyskinesia, chronic bronchitis, chronic obstructive pulmonary disease (COPD), asthma or respiratory tract infections, comprising administering to the patient a therapeutically effective amount of an antibody, or antigen-binding fragment thereof, that specifically binds to and inhibits human Notch-2, and inhibits or reduces goblet cell formation and mucus hypersecretion in the patient.

* * * * *